(12) United States Patent
Katrukha et al.

(10) Patent No.: US 10,191,066 B2
(45) Date of Patent: *Jan. 29, 2019

(54) METHOD FOR DETERMINING THE RISK OF CARDIOVASCULAR EVENTS USING IGFBP FRAGMENTS

(75) Inventors: Alexey G. Katrukha, Turku (FI); Alexander B. Postnikov, Moscow (RU); Tatiana I. Smolyanova, Moscow region (RU); Alexey V. Kharitonov, Moscow (RU); Natalia N. Tamm, Moscow (RU)

(73) Assignee: HYTEST LTD., Turku (FI)

( * ) Notice: Subject to any disclaimer, the term of this patent is extended or adjusted under 35 U.S.C. 154(b) by 233 days.

This patent is subject to a terminal disclaimer.

(21) Appl. No.: 13/823,674

(22) PCT Filed: Apr. 13, 2012

(86) PCT No.: PCT/FI2012/050365
§ 371 (c)(1),
(2), (4) Date: May 21, 2013

(87) PCT Pub. No.: WO2012/140327
PCT Pub. Date: Oct. 18, 2012

(65) Prior Publication Data
US 2014/0017714 A1    Jan. 16, 2014

Related U.S. Application Data

(60) Provisional application No. 61/475,778, filed on Apr. 15, 2011.

(30) Foreign Application Priority Data

Apr. 15, 2011   (FI) .................................... 20115367

(51) Int. Cl.
*G01N 33/68* (2006.01)
*A61K 38/17* (2006.01)

(52) U.S. Cl.
CPC ..... *G01N 33/6893* (2013.01); *A61K 38/1754* (2013.01); *G01N 2333/4745* (2013.01);
(Continued)

(58) Field of Classification Search
CPC ............... A61K 38/1754; C07K 16/18; C07K 2317/33; C07K 2317/34; G01N 33/6893;
(Continued)

(56) References Cited

U.S. PATENT DOCUMENTS 7,115,382 B1 * 10/2006 Overgaard et al. ............ 435/7.4
9,012,610 B2 *  4/2015 Katrukha et al. .......... 530/387.9
(Continued)

FOREIGN PATENT DOCUMENTS

CN            1553194 A      12/2004
CN         101206225 A       6/2008
(Continued)

OTHER PUBLICATIONS

Laursen et al., 2001. Pregnancy-associated plasma protein-A (PAPP-A) cleaves insulin-like growth factor binding protein (IGFBP)-5 independent of IGF: implications for the mechanism of IGFBP-4 proteolysis by PAPP-A. FEBS Lett. 504: 36-40.*
(Continued)

*Primary Examiner* — Gailene R Gabel
(74) *Attorney, Agent, or Firm* — Birch, Stewart, Kolasch & Birch, LLP

(57) ABSTRACT

The present invention describes the method for determining the risk of future major adverse cardiovascular events, which comprises detection proteolytic fragments of IGFBP-4 or IGFBP-5 (insulin-like growth factor binding protein 4 or insulin-like growth factor binding protein 5) in patients'
(Continued)

blood. The present invention provides antibodies and immunoas-says, suitable for specific measurement of proteolytic fragments of IGFBPs. In current invention the IGFBP fragments are suggested to be utilized as blood biomarkers for the risk prediction of major adverse cardiovascular events (MACE).

11 Claims, 11 Drawing Sheets
(11 of 11 Drawing Sheet(s) Filed in Color)
Specification includes a Sequence Listing.

(52) U.S. Cl.
CPC . *G01N 2800/2871* (2013.01); *G01N 2800/32* (2013.01); *G01N 2800/52* (2013.01); *G01N 2800/60* (2013.01)

(58) Field of Classification Search
CPC ... G01N 2333/4745; G01N 2800/2871; G01N 2800/32; G01N 2800/52; G01N 2800/60
See application file for complete search history.

(56) References Cited

U.S. PATENT DOCUMENTS

| | | | |
|---|---|---|---|
| 2010/0136711 A1* | 6/2010 | Yoshimura et al. | 436/501 |
| 2010/0285491 A1 | 11/2010 | Wienhues-Thelen et al. | |

FOREIGN PATENT DOCUMENTS

| | | | | |
|---|---|---|---|---|
| WO | WO 02/056015 A1 | 7/2002 | | |
| WO | WO 2006/086891 | * | 8/2006 | ............ A61K 38/17 |
| WO | WO 2007/053589 A2 | 5/2007 | | |
| WO | WO 2011/001029 A1 | 1/2011 | | |

OTHER PUBLICATIONS

Ständker et al., 2000. Partial IGF affinity of circulating N- and C-terminal fragments of human insulin-like growth factor binding protein-4 (IGFBP-4) and the disulfide bonding pattern of the C-terminal IGFBP-4 domain. Biochem. 39: 5082-5088.*
Štulc et al., 2003. increased levels of pregnancy-associiated plasma protein-A in patients with hypercholesterolemia: the effect of atorvastatin treatment. Am. Heart J. 146: e21, pp. 1-4.*
Fosang et al., 2003. Neoepitopes as biomarkers of cartilage catabolism. Inflamm. Res. 52: 277-282.*
Qin et al., 2005. Molecular distinction of circulating pregnancy-associated plasma protein A in myocardial infarction and pregnancy. Clin. Chem. 51: 75-83.*
Forssmann et al. DE 19757250 (Abstract) Jul. 1, 1999.*
Standker et al. Partial IGF Affinity of Circulating N- and C-Terminal Fragments of Human Insulin-like Growth Factor Binding Protein (IGFBP-4) and the Disulfide Bonding Pattern of the C-Terminal IGFBP-4 Domain. Biochemistry 39: 5082-5088 (2000).*
Chernausek et al., "Proteolytic Cleavage of Insulin-like Growth Factor Binding Protein 4 (IGFBP-4)", The Journal of Biological Chemistry, vol. 270, No. 19, Issue of May 12, pp. 11377-11382, 1995.
Conover et al., "Cleavage Analysis of Insulin-like Growth Factor (IGF)-dependent IGF-binding Protein-4 Proteolysis and Expression of Protease-resistant IGF-binding Protein-4 Mutants", The Journal of Biologial Chemistry, vol. 270, No. 9 Issue of Mar. 3, pp. 4395-4400, 1995.
Consuegra-Sanchez et al., "Pregnancy-associated plasma protein-A (PAPP-A) and cardiovascular risk", Atherosclerosis, vol. 203, pp. 346-352, 2009.
Finnish Search Report, dated Jan. 24, 2012, issued in Finnish Priority Application 20115367.
Fischer et al., "Associations of insulin-like growth factor binding proteins and acid-labile subunit with coronary heart disease", Clinical Endocrinology, vol. 61, pp. 595-802, 2004.
International Search Report, dated Jul. 7, 2012, issued in PCT/IF2012/050365.
Piñon et al., "Imflammation, Atherosclerosis, and Cadiovascular Disease Risk: PAPP-A, Lp-PLA2, and Cystatin C. New Insigths or Redundant Information?", Review Article, vol. 59, No. 3, pp. 247-258, 2006.
Postnikov et al., "N-terminal and C-terminal fragments of IGFBP-4 as novel biomarker for short-term rist assessment of major adverse cardiac events in patients presenting with ischemia", Clinical Biochemistry vol. 45, pp. 519-524, 2012.
Prentice et al., "Novel proteins associated with risk for coronary heart disease or stroke among postmenopausal women Identified by in-depth plasma proteose profiling", Gnome Medicine, No. 2, vol. 48, pp. 1-13, 2010.
Written Opinion of the International Searching Authority, dated Jul. 7, 2012, issued in PCT/IF2012/050365.
Chinese Search Report for Chinese Application No. 201280029310.5, dated Nov. 14, 2014 (English translation provided only).
Extended European Search Report for European Application No. 12770850,1, dated Oct. 13, 2014.
Khosravi et al., "Pregnancy associated plasma protein-A: ultrasensitive immunoassay and determination in coronary heart disease," Clinical Biochemistry, vol. 35, No. 7, Oct. 2002, pp. 531-538, XP-001188913.

* cited by examiner

US 10,191,066 B2

METHOD FOR DETERMINING THE RISK OF CARDIOVASCULAR EVENTS USING IGFBP FRAGMENTS

This application is the National Phase of PCT/FI2012/050365 filed on Apr. 13, 2012, which claims priority under 35 U.S.C. 119(e) to U.S. Provisional Application No. 61/475,778 filed on Apr. 15, 2011, and under U.S.C. 119(a) to Patent Application No. 20115367 filed in Finland on Apr. 15, 2011, all of which are hereby expressly incorporated by reference into the present application.

FIELD OF THE INVENTION

The present invention describes the method for determining the risk of future major adverse cardiovascular events, which comprises detection proteolytic fragments of IGFBP-4 or IGFBP-5 (insulin-like growth factor binding protein 4 or insulin-like growth factor binding protein 5) in patients' blood. The present invention provides antibodies and immunoassays, suitable for specific measurement of proteolytic fragments of IGFBPs. In the current invention the IGFBP fragments are suggested to be utilized as blood biomarkers for the risk prediction of major adverse cardiovascular events (MACE).

BACKGROUND OF THE INVENTION

Despite considerable advances in the treatment of cardiovascular disease, it remains the leading cause of death in developed countries. Assessment of classic cardiovascular risk factors—including high blood pressure, diabetes and smoking—has a central role in disease prevention. However, many individuals with coronary heart disease (a narrowing of the blood vessels that supply the heart) have only one, or none, of the classic risk factors. Thus, new biomarkers are needed to augment the information obtained from traditional indicators and to illuminate disease mechanisms.

The search for reliable biomarkers of future MACE risk assessment seems to be significant task of modern in vitro diagnostics. MACE comprises acute coronary syndrome (ACS), unstable angina pectoris, myocardial infarction (MI) comprising ST-elevation MI and non-ST-elevated MI and some other events. In spite of wide group of candidates to be used for MACE risk assessment, described in literature, none of them became a gold standard biomarker such as cardiac Troponin I (cTnI) for myocardial infarction or NT-proBNP for heart failure diagnosis. The major disadvantages of the biomarkers of MACE risk assessment used in the clinical practice are insufficient cardiovascular specificity, unobvious relationship between the blood levels of analyte and oncoming cardiovascular complications, and as a result—limited prognostic value. There is an urgent need for biomarkers that could be used in emergency department for the MACE risk assessment of patients with acute chest pain without clear signs of acute myocardial infarction (having negative Troponin tests and no ST-elevation on an electrocardiogram). Such biomarker could also open up a possibility to screen the group of patients having classic cardiovascular risk factors to identify the subgroup of higher risk of short-term cardiac events.

Studies of inflammatory biomarkers related to atherosclerotic plaques destabilization has opened up a new prospective in the risk assessment of MACE. Wide family of candidate biomarkers (high-sensitivity C-reactive protein (hsCRP), Lipoprotein-associated Phospholipase A2 (Lp-PLA2), Matrix Metalloproteinase-9, Monocyte Chemotactic Protein-1, Soluble CD40L, Myeloperoxidase, etc.) has been intensively investigated during the last decade. Sufficient published evidence has been accumulated to support the utility of two of them—hsCRP and Lp-PLA2 in clinical practice.

In the present invention the fragments of IGFBP-4 and IGFBP-5 are proposed as biomarkers for MACE prediction. Specific proteolysis is a major regulatory mechanism of IGFBP-4 and IGFBP-5 function. Pregnancy-associated plasma protein-A (PAPP-A) was described in literature as an enzyme, responsible for the IGFBP-4 and IGFBP-5 proteolysis and subsequent release of active IGFs. Despite of proteolytic activity of PAPP-A inside of atherosclerotic plaque was not proved, it was speculated that in atherosclerotic plaques PAPP-A expressed by activated smooth muscle cells enhances IGF's bioavailability. We suggest using proteolytic fragments of IGFBP-4 and IGFBP-5 as independent blood biomarkers that could be used for the prediction of MACE.

SUMMARY OF THE INVENTION

The present invention describes a method for determining the risk of future major adverse cardiovascular events, which comprises detection of proteolytic fragments of IGFBP-4 or IGFBP-5 (insulin-like growth factor binding protein 4 or 5) in patients' blood. The method enables classifying the individuals in different risk groups according to the values of the measured N-terminal fragment of IGFBP-4 or C-terminal fragment of IGFBP-4, as well as N-terminal fragment of IGFBP-5 or C-terminal fragment of IGFBP-5. In the method an increase of N-terminal fragment of IGFBP-4 or C-terminal fragment of IGFBP-4, as well as N-terminal fragment of IGFBP-5 or C-terminal fragment of IGFBP-5 is associated with increased risk of major adverse cardiovascular events. The present invention provides antibodies and immunoassays, suitable for specific measurement of proteolytic fragments of IGFBP-4 and also antibodies and immunoassays, suitable for specific measurement of N-terminal fragment of IGFBP-5. Antibodies specific to novel proteolytic epitopes formed in the process of proteolytic cleavage of IGFBP-4 or IGFBP-5 (proteolytic neo-epitopes) are suitable for the precise immunodetection of both N- and C-terminal fragments of IGFBP-4 as well as N-terminal fragment of IGFBP-5 in human blood irrespective of the presence of full-length IGFBP-4 and IGFBP-5 molecules. The present invention also provides a method for differential detection of IGFBP-4 based on separate measurements of full-length IGFBP-4 and total full-length IGFBP-4 and the fragments of IGFBP-4. The concentration of IGFBP-4 fragments was further calculated as a difference of total and full-length IGFBP-4.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION OF THE INVENTION

Figure 1:
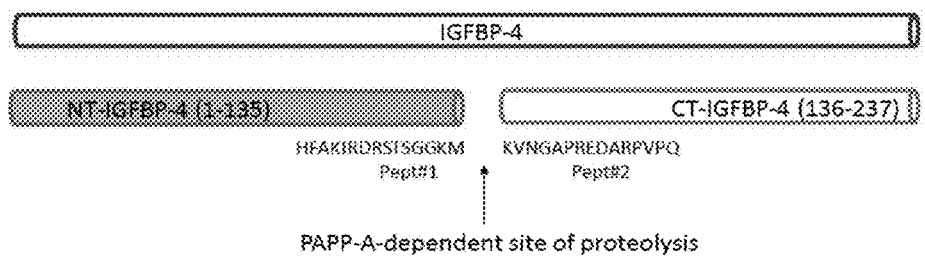
FIG. 1. Description of synthetic peptides and antigens obtained for mice immunization and testing.
Immunogens: 1. full-length IGFBP-4 produced in NSO cells,
   2. IGFBP-4-Peptide#1 (SEQ ID NO: 11), conjugated with BSA
   3. IGFBP-4-Peptide#2 (SEQ ID NO: 12), conjugated with BSA FIG. 2. Schematic illustration of the specificity of selected monoclonal antibodies.

In the experiments made for the present invention the levels of NT-IGFBP-4 and CT-IGFBP-4 fragments in the plasma of patients with acute myocardial infarction were 5.1 and 2.7-fold higher, respectively, than in plasma of healthy donors. The results of this initial clinical study open the possibility to explore the value of IGFBP-4 fragments for MACE risk assessment.

The prognostic value of IGFBP-4 proteolytic fragments as well as N-terminal fragment of IGFBP-5 was assessed in prospective follow-up clinical study. Consecutive patients admitted to emergency department with acute chest pain and tightness of breath were included in the study. IGFBP-4 fragments and N-terminal fragment of IGFBP-5 were measured in the plasma of patients. During 6 months follow-up the incidence of MACE was observed. As a result the increased levels of both N- and C-terminal fragments of IGFBP-4 and N-terminal fragment of IGFBP-5 in patients' samples were associated with significant increase of MACE risk.

IGFBP-4 fragments can fulfil an apparently unmet need of a blood assay that can predict short-term risk of MACE.

In the present invention the detection antibodies of developed sandwich immunoassay methods were labeled by stable Eu3+ chelate. In various other embodiments detection antibody could be labeled by different types of labels able to generate different types of signals that could be visualized or detected using a variety of standard procedures, such as detection of luminescence, chemiluminescence, fluorescence, absorbance, radioactivity, or by microscopy, imaging, etc. Immunoassays may include immunohistochemistry, enzyme-linked immunosorbent assay (ELISA), Western blotting, nephelometry, turbidimetry, immunoradiometric assay, lateral flow, immunohisto/cyto-chemistry and other methods known to those of skill in the art.

In the present invention atherosclerotic form of PAPP-A was shown to cleave IGFBP-4 with the same efficiency as recombinant PAPP-A (Example 6). Thus, for the first time it was shown that atherosclerotic form of PAPP-A expressed in human plaques is an active protease that is able to cleave IGFBP-4.

Immunoassays could be used to determine presence or absence of a biomarker in a sample as well as the amount of a biomarker in a sample. The amount of IGFBP-4 proteolytic fragments in the sample can be determined by comparison to (or as a ratio to) a reference or standard, such as an intact IGFBP-4 or different polypeptide known to be present in the sample. The amount of IGFBP-4 proteolytic fragments in the sample can also be determined by comparison to a reference or standard, such as the amount of the endogenous or recombinant or synthetic IGFBP-4 fragments in a reference or control sample. Accordingly, the amount of a biomarker in a sample need not be quantified in absolute terms, but may be measured in relative terms with respect to a reference or control.

Various embodiments of this invention include detection of N-terminal or C-terminal, or simultaneous C-terminal and N-terminal fragments of IGFBP-4 in the patients' plasma samples for the assessment of ACS development risk.

Immunoassays could be used to determine presence or absence of a biomarker in a sample as well as the amount of a biomarker in a sample. The amount of IGFBP-4 proteolytic fragments in the sample can be determined by sandwich immunoassay specific to proteolytic fragments of IGFBP-4, such as a difference in quantity of total IGFBP-4

(full-length and fragment of IGFBP-4) and full-length IGFBP-4. The present study shows the possibility to use such calculations for quantitative measurements of NT- and CT-IGFBP-4 fragments (Example 9).

EXPERIMENTAL

Example 1. Generation of Mouse Monoclonal Antibodies Specific to Novel Proteolysis-Mediated Epitopes of IGFBP-4

Synthetic Peptides Obtained for Mice Immunization:

```
IGFBP-4 Peptide-1 (SEQ ID NO: 7): CHFAKIRDRSTSGGKM;

IGFBP-4 Peptide-2 (SEQ ID NO: 12): KVNGAPREDAR-
PVPQC.
```

IGFBP-4 Peptide-1 (SEQ ID NO: 11) and IGFBP-4 Peptide-2 (SEQ ID NO: 12) (FIG. 1) were synthesized using solid-phase Fmoc chemistry. Peptides were prepared on p-alkoxybenzylalcohol resin. After cleavage from the resin, the crude peptide preparation was purified by reversed-phase high-pressure liquid chromatography.

C18 preparative column was applied with a gradient of 0.1% trifluoroacetic acid in water and 0.1% trifluoroacetic acid in acetonitrile. The purity (>95%) was determined by analytical C18 high-pressure liquid chromatography and mass spectroscopy (matrix-assisted laser desorption/ionization mass spectrometry with accuracy±0.5 Dalton).

IGFBP-4 Peptide-1 contained the amino acid sequence identical to IGFBP-4 fragment 122-135 with one additional cysteine residue from the N-terminus. IGFBP-4 Peptide-2 contained the amino acid sequence identical to IGFBP-4 fragment 136-150 with one additional cysteine residue from the C-terminus. Sulphhydryl groups of these additional cysteine residues were used for the preparation of the peptide conjugates with carrier proteins.

Preparation of conjugates of the peptides with carrier proteins was performed by using sulfo-SMCC obtained from Pierce (Rockford, Ill.) according to manufacturer's instructions. For the conjugation 2.5 mg of carrier protein-bovine serum albumin (BSA) or ovalbumin (both obtained from Sigma Chemicals, St. Louise, Mo.) was dissolved in 10 mM $KHPO_4$, 150 mM NaCl, pH 7.4 (PBS) to the concentration 10 mg/ml. Two milligrams of sulfo-SMCC, dissolved in 0.1 ml dimethyl sulfoxide, were added to the protein solution. Reaction of carrier protein activation was carried out for 2 hours at room temperature. Excess of sulfo-SMCC was removed by gel-filtration using NAP-5 columns (obtained from GE Healthcare Life Sciences, Piscataway, N.J.). NAP-5 columns were pre-equilibrated with 10 mM $KH_2PO_4$, 150 mM NaCl, pH 7.2. Then 2 mg of synthetic peptide-1 or peptide-2 were added to protein solution to start the conjugation. This reaction was carried out for 2 hours on ice with constant shaking. Unreacted peptide fraction was removed from protein-peptide conjugate by using gel-filtration NAP-5 columns, pre-equilibrated with PBS. The conjugation of the peptides to appropriate carrier protein was confirmed by 3-5 kDa increase in the protein molecular weight revealed by using sodium dodecyl sulphate polyacrylamide gel electrophoresis. Conjugates were aliquoted and stored at −20° C. until use.

Immunization of Mice with Peptide-(Carrier Protein) Conjugates

Groups of five BALB/c mice were immunized five times with peptide-protein conjugates.

Group 1: First immunization: intraperitoneally 0.2 ml of 10 μg BSA-Peptide-1 in PBS with 60% Freund's complete adjuvant; Second immunization: on day 30, intraperitoneally 0.2 ml of 5 μg BSA-Peptide-1 in PBS with 60% Freund's incomplete adjuvant; Third immunization: on day 60, intraperitoneally 0.2 ml of 2.5 μg BSA-Peptide-1 in PBS.

Group 2: First immunization: intraperitoneally 0.2 ml of 10 μg BSA-Peptide-2 in PBS with 60% Freund's complete adjuvant; Second immunization: on day 30, intraperitoneally 0.2 ml of 5 μg BSA-Peptide-2 in PBS with 60% Freund's incomplete adjuvant; Third immunization: on day 60, intraperitoneally 0.2 ml of 2.5 μg BSA-Peptide-2 in PBS.

Twenty days after third immunization mice with the highest titer of peptide-specific antibodies were selected for the last immunizations and hybridization. Mice were intravenously injected with 0.2 ml of 10 μg BSA-Peptide-1 in PBS for Group 1 and with 0.2 ml of 10 μg BSA-Peptide-2 in PBS for Group 2. Intravenous injections were repeated next day at the same protocol (fifth immunization). Then two days after the fifth immunization, spleens of immunized mice were sterilely isolated and homogenized tissue was fused with the mouse myeloma cell line sp2/0 as described previously (Köhler and Milstein, 1975, 1976; Köhler et al., 1976; Hammerling et al., 1981).

Conditioned culture of growing hybridomas was screened for antibodies by enzyme linked immunosorbent assay (ELISA). Hybridomas that produced antibodies specific to Peptide-1 or Peptide-2 were selected by ELISA with ovalbumin-Peptide-1 or ovalbumin-Peptide-2, respectively, used as preadsorbed antigens. Human recombinant IGFBP-4 expressed in NSO cell line (obtained from Sigma Chemicals, St. Louise, Mo.) was used as well as a preadsorbed antigen for the additional test. For the assay 50 ng/0.1 ml PBS per well of ovalbumin-Peptide-1, or ovalbumin-Peptide-2, or human recombinant IGFBP-4 were adsorbed onto the immunoassay polystyrene plates (obtained from Corning, Cambridge, Mass.). After 40 min of antigen sorption the plates were washed two times and blocked for 10 min with PBS, containing detergent Tween20, 0.1% (PBST). Then the plates were incubated with 0.05 ml of conditioned media collected from growing hybridomas for 30 min and washed two times with PBST. Mouse antibodies bound to preadsorbed antigens were revealed by 30 min incubation with secondary anti-mouse IgG polyclonal antibodies, conjugated with HRP, 0.1 ml of 1:1000 dilution in PBST per well. Secondary antibodies were from Sigma Chemicals, St. Louise, Mo. After the incubation with secondary antibodies the plates were washed with PBST six times and 3,3',5,5'-tetramethyl benzidine (TMB) peroxidase substrate, containing 0.03% hydrogen peroxide, was added. The reaction was stopped after 15 minutes of incubation by adding 0.1 ml of 0.5 M phosphoric acid and absorbance in wells was measured at 450 nm. The measurement of the absorbance was performed with the Labsystems Multiscan microplate reader (Labsystems, Finland).

Hybridomas producing antibodies specific to appropriate peptide, conjugated with ovalbumin (Absorbance at described above conditions at 450 nm>0.5 over background), and at the same time not reacting with human recombinant IGFBP-4 (Absorbance at 450 nm<0.025 over background), were selected for further work. Such hybridomas were cloned by limiting dilution. Hybridoma clones secreting the monoclonal antibodies of interest were grown in Dulbecco's modified Eagle's medium (DMEM), containing 10% fetal bovine serum (HyClone Laboratories, Logan, Utah).

Affinity Purification of Antibodies

Monoclonal antibodies were raised in mouse ascitic fluid after intraperitoneal injection of selected hybridoma clones. Antibodies were purified from ascitic fluid by using Protein A affinity chromatography. The resin was from GE Healthcare Life Sciences (Piscataway, N.J.), and purification was carried out according to manufacturer's instructions. Purified monoclonal antibodies were stored as suspensions in 50% ammonium sulfate at 4° C.

Investigation of Specificity of Monoclonal Antibodies

Figure 2:
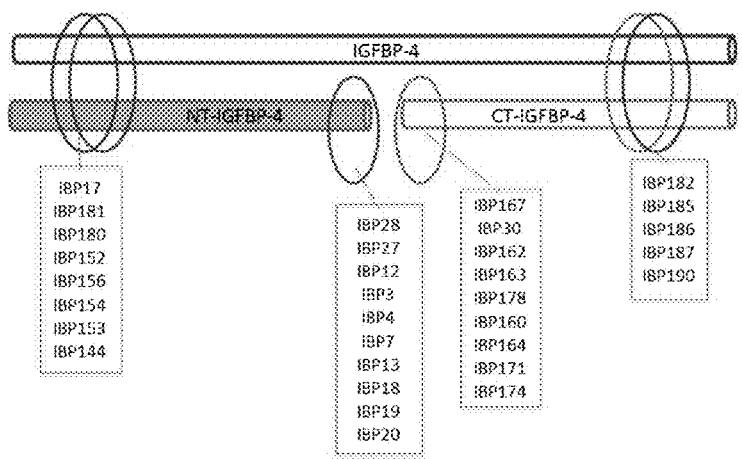
Figure 6:
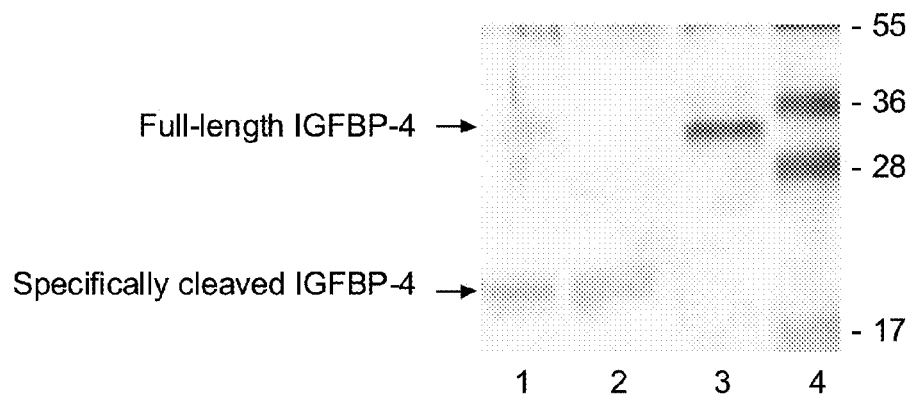
FIG. 6. Western blotting detection of proteolytic fragments of IGFBP-4 demonstrating PAPP-A protease activity. Rabbit anti-IGFBP-4 polyclonal antibodies were used for immunostaining.
IGFBP-4 (200 ng per lane) was treated by:
Lane 1, recombinant PAPP-A;
Lane 2, atherosclerotic tissue PAPP-A;
Lane 3, without PAPP-A;
Lane 4, Molecular weight standards; shown in kDa.

To confirm the specificity of selected monoclonal antibodies IGFBP-4 proteolytic fragments were obtained. PAPP-A-dependent proteolytic reaction was performed according to conditions described earlier (Overgaard et al., 2000). Two µg of human recombinant IGFBP-4 was incubated in 0.23 ml of 50 mM Tris-HCl, pH 7.5, in the presence of 2 mM $CaCl_2$, 1.8 µg IGF-II (obtained from Sigma Chemicals, St. Louise, Mo.). 40 ng of human recombinant PAPP-A (HyTest, Turku, Finland), and 2 microliters protease inhibitors cocktail (obtained from Sigma Chemicals, St. Louise, Mo.). The reaction was carried out for 15 hours at 37° C., and was stopped by freezing the sample at −20° C. The degree of PAPP-A-dependent cleavage of IGFBP-4 was determined by Western blotting by using 1 µg/ml specific rabbit polyclonal antibodies obtained from Abcam (Cambridge, Mass.) (FIG. 6). Specificity studies of selected monoclonal antibodies to IGFBP-4 proteolytic fragments were performed in indirect ELISA using affinity-purified antibodies. Ten ng of full-length recombinant IGFBP-4 or IGFBP-4 fragments produced by PAPP-A-dependent cleavage (preparation described above) were sorbed on polystyrene plate. After 40 min of incubation the plates were washed two times and blocked for 10 min with PBS, containing detergent Tween 20, 0.1% (PBST). Then selected MAbs (10 µg/ml) were incubated for 30 min at room temperature with shaking and after that washed two times with PBST. Specifically bound antibodies were detected by anti-mouse IgG polyclonal antibodies, conjugated with HRP, 0.1 ml of 1:1000 dilution in PBST per well. Secondary antibodies were from Sigma Chemicals, St. Louise, Mo. After incubation with secondary antibodies the plates were washed with PBST six times and 3,3',5,5'-tetramethyl benzidine (TMB)-containing peroxidase substrate, supplemented with 0.03% hydrogen peroxide, was added. The reaction was stopped after 15 minutes of incubation by adding 0.1 ml of 0.5 M phosphoric acid and absorbance was measured at 450 nm. The group of monoclonal antibodies specific to proteolytic fragments of IGFBP-4, produced by PAPP-A-dependent cleavage, and having cross-reactivity to intact IGFBP-4 less than 5% was finally selected: IBP28, IBP27, IBP12, IBP3, IBP4, IBP7, IBP13, IBP18, IBP19, IBP20, IBP30, IBP167, IBP174, IBP160, IBP161, IBP164, IBP171, IBP163, IBP162 (FIG. 2). All monoclonal antibodies were of IgG isotype, except that IBP30 was of IgM isotype.

Example 2. Generation of Mouse Monoclonal Antibodies Specific to Intact IGFBP-4

Immunization of Mice

Five BALB/c mice were immunized five times with human recombinant IGFBP-4 expressed in mammalian NSO cell line. The protein was obtained from Sigma Chemicals, St. Louise, Mo. First immunization: intraperitoneally 0.2 ml of 5 µg IGFBP-4 in PBS with 60% Freund's complete adjuvant. Second immunization: on day 30, intraperitoneally 0.2 ml of 2 µg IGFBP-4 in PBS with 60% Freund's incomplete adjuvant. Third immunization: on day 60, intraperitoneally 0.2 ml of 2 µg IGFBP-4 in PBS.

Twenty days after third immunization mice with the highest titer of protein-specific antibodies were selected for the following immunizations and hybridization. The mice were intravenously injected for a fourth time with 0.2 ml of 2 µg IGFBP-4 in PBS. The last intravenous injection was performed on the next day according to the same protocol (fifth immunization). Two days later, spleen of immunized mice was sterilely isolated and homogenized tissue was fused with the mouse myeloma cell line sp2/0 as described previously (Köhler and Milstein, 1975, 1976; Köhler et al., 1976; Hammerling et al., 1981). Conditioned media of growing hybridomas was screened for IGFBP-4-specific antibodies using ELISA method. Hybridomas producing antibodies specific to intact IGFBP-4 were selected by means of indirect ELISA. For the assay 50 ng/0.1 ml PBS per well of full-length human recombinant IGFBP-4 were sorbed on the immunoassay polystyrene plates. After 40 min of incubation the plates were washed two times and blocked for 10 min with PBS, containing detergent Tween 20, 0.1% (PBST). Then the plates were incubated for 30 min with 0.05 ml of conditioned media collected from wells containing growing hybridomas. After incubation the plates were washed two times with PBST. After washing the plates were incubated with 0.1 ml of per well of secondary anti-mouse IgG polyclonal antibodies, conjugated with HRP (1:1000 dilution in PBST) for 30 min. After incubation with secondary antibodies the plates were washed with PBST six times and peroxidase substrate, containing TMB and 0.03% hydrogen peroxide, was added. The reaction was stopped after 15 minutes of incubation by adding 0.1 ml of 0.5 M phosphoric acid and the absorbance in wells was measured at 450 nm. Hybridomas producing antibodies specific to full-length IGFBP-4 (absorbance at described above conditions at 450 nm>0.5 over background) were cloned by limiting dilution method. Hybridoma clones secreting the monoclonal antibodies of interest were cultivated in DMEM, containing 10% fetal bovine serum.

Affinity Purification of Antibodies

Monoclonal antibodies specific to full-length IGFBP-4 were raised in mouse ascitic fluid after intraperitoneal injection of selected hybridoma clones. Antibodies were purified from ascitic fluid by using Protein A affinity chromatography. The resin was from GE Healthcare Life Sciences (Piscataway, N.J.), and purification was carried out according to manufacturer's instructions. Purified monoclonal antibodies were stored as suspensions in 50% ammonium sulfate at 4° C. The group of monoclonal antibodies specific to intact (full-length) IGFBP-4, was finally selected: IBP17, IBP180, IBP181, IBP153, IBP154, IBP152, IBP156, IBP144, IBP190, IBP182, IBP185, IBP186, IBP187 (FIG. 2).

Figure 3:
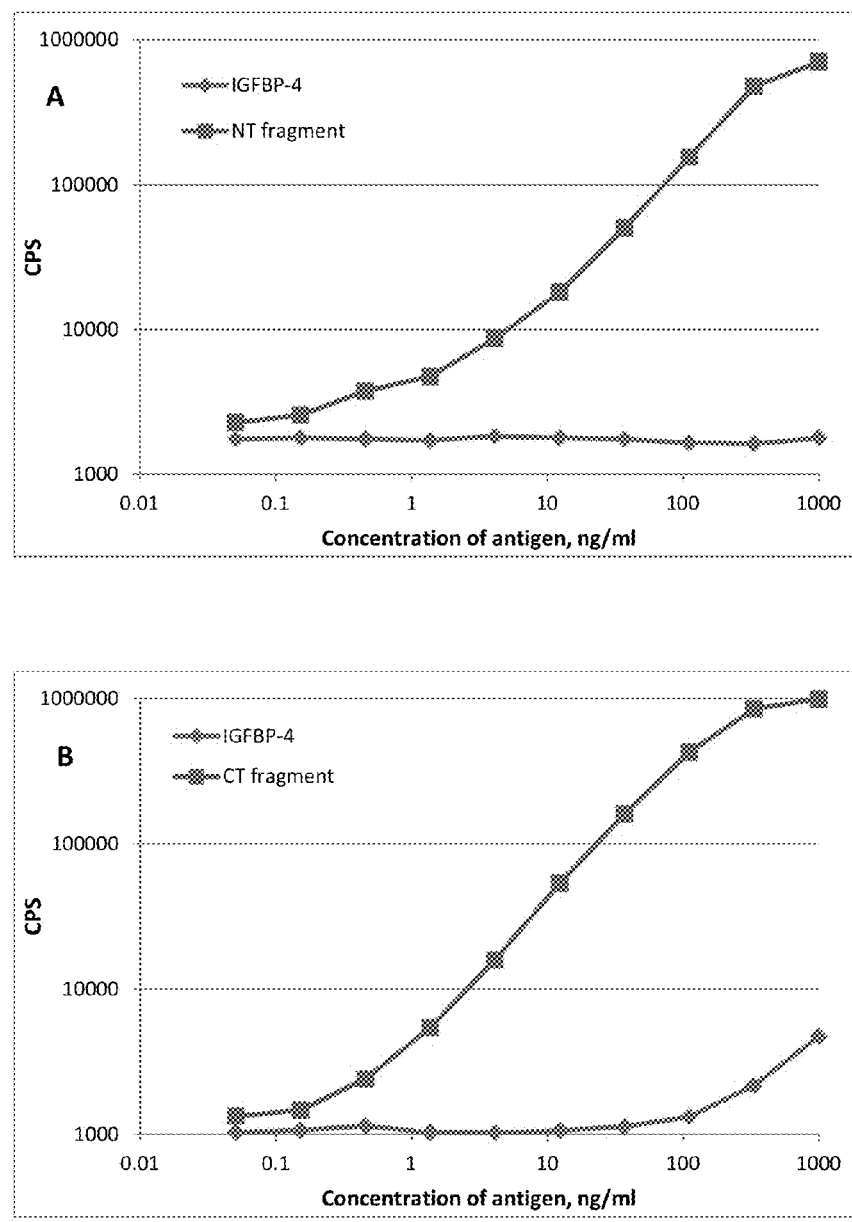
FIGS. 3A and 3B. Calibration curves of sandwich immunoassays specific to NT-IGFBP-4 proteolytic fragments (A, immunoassay IBP3-IBP144) and CT-IGFBP-4 proteolytic fragments (B, immunoassay IBP182-IBP163) and their cross-reaction with full-length IGFBP-4.

Example 3. Design of Sandwich Immunoassays for Quantification of IGFBP-4 Fragments Specificity of affinity-purified monoclonal antibodies was also checked in sandwich immunoassays (FIG. 3). Several groups of specific antibodies were tested in sandwich immunoassay in order to find combinations with required properties. Monoclonal antibodies specific to proteolytic neo-epitopes were tested with monoclonal antibodies specific to the intact (full-length) IGFBP-4 to develop sandwich immunoassays for specific determination of IGFBP-4 proteolytic fragments regardless of the presence of intact (full-length) IGFBP-4. Several sandwich assays utilizing one monoclonal antibody specific to proteolytic fragment of IGFBP-4 (N- or C-terminal; cross-reaction with full-length molecule less than 5% in indirect ELISA) and another MAb, recognizing any epitope of intact IGFBP-4, were developed. Generation of mouse monoclonal antibodies specific to intact IGFBP-4 is described in Example 2. To perform sandwich fluorescent immunoassays detection MAbs labeled with stable Eu3+ chelate were used as described by Hyytiä et al., 2010. Capture antibodies in this assay were specific to intact IGFBP-4, whereas detection antibodies were specific to proteolytic neo-epitopes of IGFBP-4. Capture antibodies (IBP3, IBP18, IBP185, IBP182), 2 µg per well in 100 µL of phosphate buffer saline, were incubated in 96-well immunoassay plates for 30 min at room temperature upon constant shaking. The plates were washed with 10 mM Tris-HCl (pH 7.8) buffer, supplemented by 0.15 M NaCl, 0.025% Tween 20 and 0.5 g/L $NaN_3$ (buffer A). After washing 0.1 ml of assay buffer (50 mM Tris-HCl buffer, pH 7.7, 9 g/L NaCl, 0.01% Tween 40, 0.5% BSA and 0.5 g/L $NaN_3$), containing 100 ng/ml of full-length human recombinant IGFBP-4 or recombinant IGFBP-4 fragments were added to the plates. The plates were incubated for 30 min at room temperature with constant shaking. After washing with buffer A 0.1 ml of the solution (1 mg/L) of detection antibodies (IBP144, IBP180, IBP177, IBP163 and IBP162) in the Assay buffer were added. The plates were incubated for 30 min at room temperature with constant shaking. After washing with buffer A, 0.2 ml of Enhancement solution (1.75M NaSCN, 1M NaCl, 5% glycerol, 20% 1-propanol, 5 mM $Na_2CO_3$, 50 mM glycine-NaOH, pH 10.0) per well were added and incubated for 3 min at room temperature with gentle shaking. Fluorescence of Eu3+ was measured on a Victor 1420 multilabel counter (Wallac-Perkin Elmer). The fluorescence was expressed in counts per second (CPS). Developed sandwich immunoassays were able to detect only IGFBP-4 fragments produced by PAPP-A-dependent cleavage and had no cross-reaction (or less than 1%) with full-length IGFBP-4. The best pair specific to NT-IGFBP-4 was IBP3-IBP144 (FIG. 3A), and the best pair specific to CT-IGFBP-4 was IBP182-IBP163 (FIG. 3B). For the sandwich immunoassay specific to NT-IGFBP-4 monoclonal antibodies specific to proteolytic fragment of IGFBP-4 were used as capture antibodies and monoclonal antibodies specific to intact IGFBP-4 were used as detection antibodies, whereas in CT-IGFBP-4 immunoassay the opposite configuration was used.

Example 4. Design of Sandwich Immunoassays for Quantification of Intact (Full-Length) IGFBP-4

Figure 4:
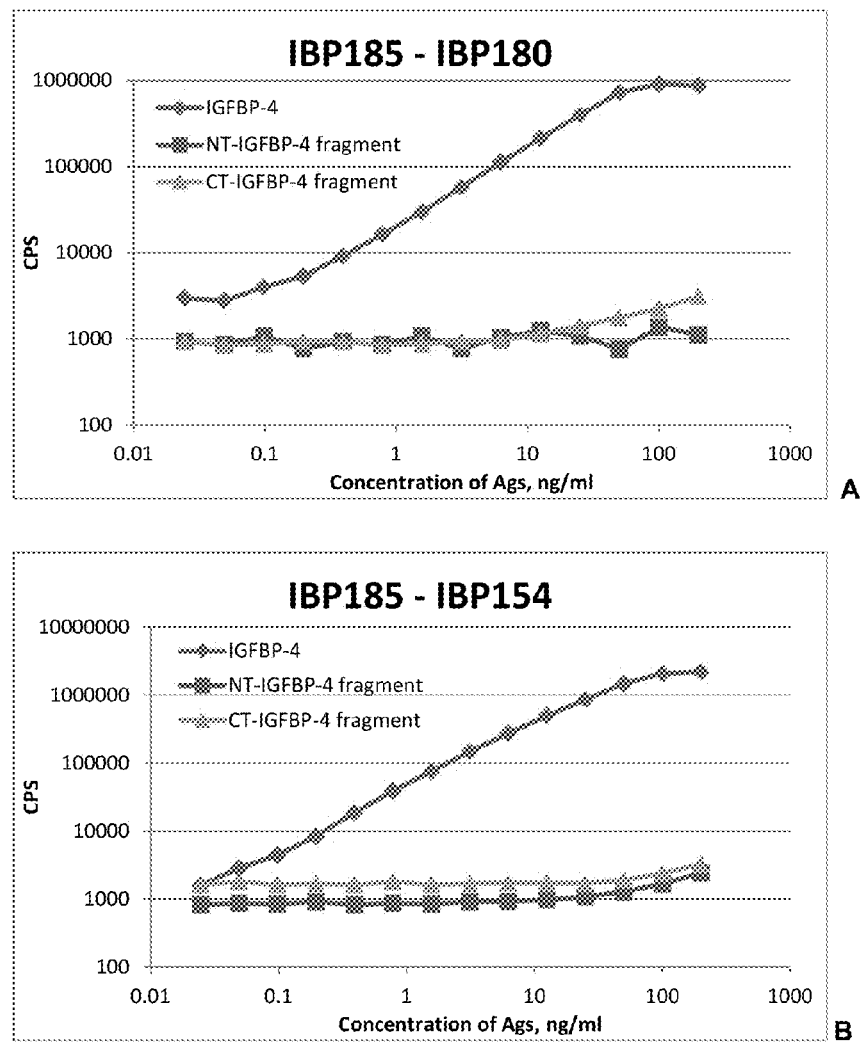
FIGS. 4A and 4B. Calibration curves of sandwich immunoassays specific to full-length IGFBP-4 (A, IBP185-IBP180 and B, IBP185-IBP154) and their cross-reaction with IGFBP-4 fragments.

Quantification of full-length IGFBP-4 in presence of IGFBP-4 fragments can be reached by using specific sandwich immunoassay utilizing one monoclonal antibody specific to N-terminal domain of protein and another MAb, recognizing epitope on C-terminal domain of intact IGFBP-4. Generation of mouse monoclonal antibodies specific to full-length IGFBP-4 is described in Example 2. To perform sandwich fluorescent immunoassays the method described in Example 3 was used. Capture antibodies in this assay were specific to C-terminal region of intact IGFBP-4 (IBP182, IBP186, IBP185, IBP187). Detection antibodies in this assay were specific to N-terminal region of full-length IGFBP-4 (IBP154, IBP180, IBP181, IBP153 and IBP156). Developed sandwich immunoassays were able to detect only full-length IGFBP-4 and have no crossreaction (or less than 1%) with fragments produced by PAPP-A-dependent cleavage. The best pairs were IBP185-IBP180 and IBP185-IBP154 (FIG. 4).

Example 5. Design of Sandwich Immunoassays for Quantification of Total IGFBP-4

Figure 5:
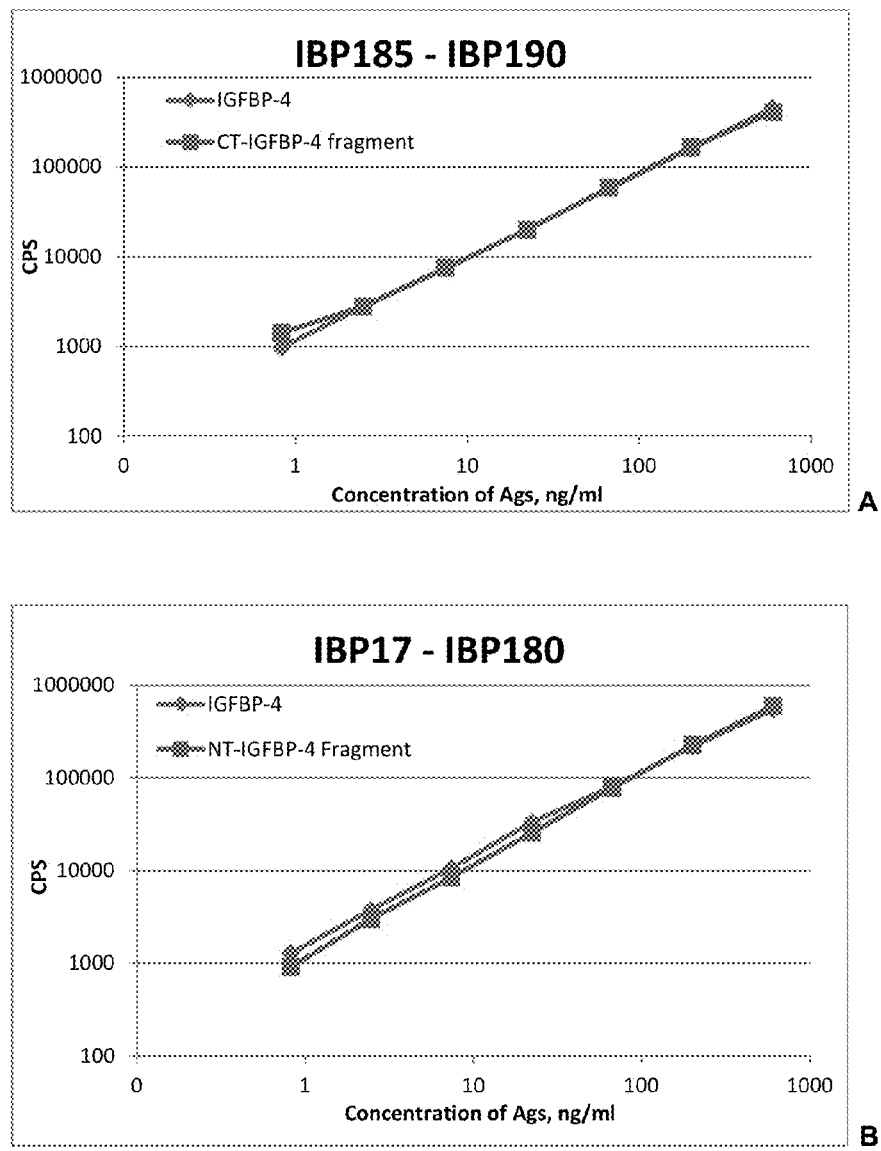
FIGS. 5A and 5B. Calibration curves of sandwich immunoassays specific to total IGFBP-4 (that recognize proteolytic fragments and full-length IGFBP-4). The assays are specific to (A) C-terminal region of IGFBP-4 (IBP185-IBP190) and (B) N-terminal region of IGFBP-4 (IBP17-IBP180); Ags—antigens.

Monoclonal antibodies specific to the both forms of IGFBP-4 (full-length and fragments) were used to develop immunoassay for detection total amounts of IGFBP-4. For such type of immunoassay it is significant to be equally specific to both form of protein: intact and proteolytic cleaved (FIG. 5). Two types of such sandwich immunoassays can be designed: (1) For detection both full-size IGFBP-4 and CT-IGFBP-4 fragment (utilizing two monoclonal antibodies recognizing epitopes in C-terminal region of IGFBP-4) and (2) for detection both full-size IGFBP-4 and NT-IGFBP-4 fragment (utilizing two monoclonal antibodies recognizing epitopes in N-terminal region of IGFBP-4). Generation of mouse monoclonal antibodies specific to intact IGFBP-4 is described in Example 2. To perform sandwich fluorescent immunoassays, we used method described in Example 3. Capture antibodies in this assay were specific to C-terminal region of intact IGFBP-4 (IBP182, IBP186, IBP185, IBP187 and IBP190). Detection antibodies in this assay were specific to N-terminal region of intact IGFBP-4 (IBP154, IBP180, IBP181, IBP153, IBP156 and IBP17). Developed sandwich immunoassays were able to detect total IGFBP-4 and have no difference (or very low-less than 10%) with fragments produced by PAPP-A-dependent cleavage and intact IGFBP-4. The best pairs were IBP185-IBP190 and IBP17-IBP180 (FIGS. 5A and 5B, respectively).

Example 6. Proteolytic Activity of Atherosclerotic Form of PAPP-A

Samples of human atherosclerotic coronary vessels were stored at −70° C. until used. PAPP-A was extracted from atherosclerotic coronary arteries after tissue homogenization. Extracted PAPP-A was purified by means of affinity chromatography. Affinity matrix used for PAPP-A purification was prepared utilizing PAPP-A-specific monoclonal antibody 4G11 (obtained from HyTest, Turku, Finland). To confirm identity of purified protein to PAPP-A, Western blotting analysis with several PAPP-A-specific monoclonal antibodies and liquid chromatography/tandem mass spectrometry analysis were used.

For proteolytic activity analysis of atherosclerotic PAPP-A 2 µg of human recombinant IGFBP-4 was incubated in 0.23 ml of 50 mM Tris-HCl, pH 7.5, in the presence of 2 mM $CaCl_2$, 1.8 µg IGF-II (obtained from Sigma Chemicals, St. Louise, Mo.), 40 ng of atherosclerotic PAPP-A, and 2 microliters protease inhibitors cocktail (obtained from Sigma Chemicals, St. Louise, Mo.). The reaction was carried out for 15 hours at 37° C., and was stopped by freezing of the sample at −20° C. The degree of PAPP-A-dependent cleavage of IGFBP-4 was determined by Western blotting using IGFBP-4-specific rabbit polyclonal antibodies (obtained from Abcam, Cambridge, Mass.) (FIG. 6).

Example 7. Measurement of IGFBP-4 Fragments in Healthy Donors and Diagnosed AMI Patients' Plasma Samples Detection of proteolytic fragments of IGFBP-4 in the plasma samples of ACS was carried out using sandwich immunoassays specific to proteolytic fragments. Blood of 43 patients with ACS (with ST-segment elevation on an electrocardiogram) as well as plasma samples from 54 healthy donors were tested by fragment-specific sandwich immunoassays IBP3-IBP144 (specific to the N-fragment) and IBP182-IBP163 (specific to the C-fragment). All plasma samples were collected from the patients in the presence of EDTA and were stored at −70° C. before measurements.

Figure 7:
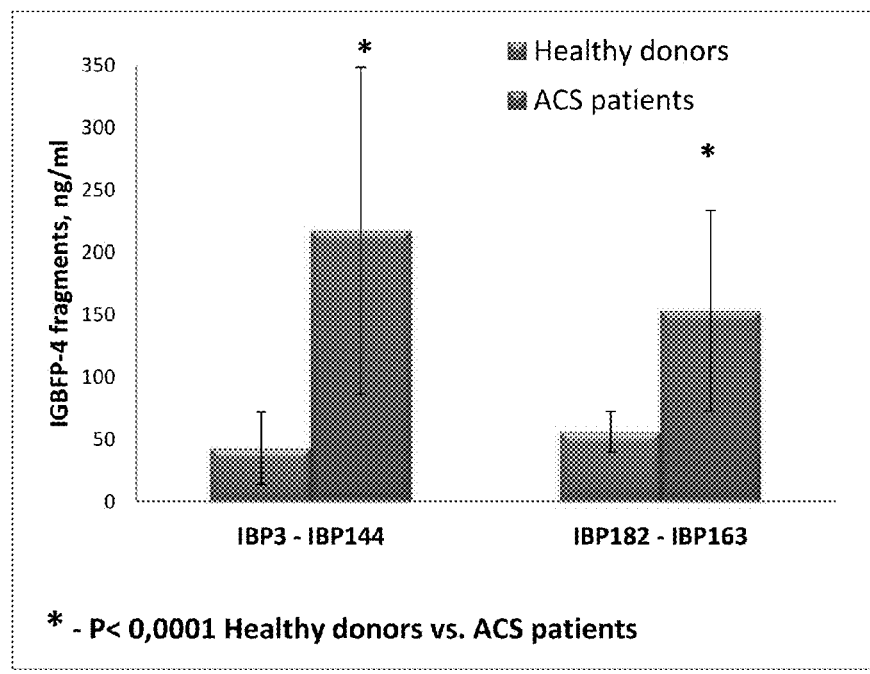
FIG. 7. Measurement of IGFBP-4 fragments in healthy donors and diagnosed AMI patients' plasma samples using sandwich immunoassays NT-IGFBP-4 and CT-IGFBP-4 (IBP3-IBP144 and IBP182-IBP163, respectively). The levels of IGFBP-4 fragments in the plasma of ACS (Acute Myocardial infarction) patients (mean±SD) was 5.1-fold higher for NT-IGFBP-4 ($p<0.0001$) and 2.7-fold higher for CT-IGFBP-4 ($p<0.0001$) than in plasma of healthy donors.

For the sandwich immunoassays capture antibody IBP3 and IBP182, 2 µg per well in 0.1 ml of phosphate buffer saline, was incubated in 96-well immunoassay plates for 30 min at room temperature upon constant shaking. After washing with buffer A, 0.1 ml of patients' plasma samples diluted 1:5 with the Assay buffer were added to the plates. Plates were incubated for 30 min at room temperature with constant shaking. After washing with buffer A 0.1 ml detection antibody IBP144 or IBP163, conjugated with stable Eu3+ chelate in the Assay buffer was added. The plates were incubated for 30 min at room temperature with constant shaking. After washing with buffer A, 0.2 ml of Enhancement solution per well was added and incubated for 3 min at room temperature with gentle shaking. Fluorescence of Eu3+ was measured using a Victor 1420 multilabel counter (Wallac-Perkin Elmer). The level of IGFBP-4 fragments in the plasma of ACS patients was 5.1 and 2.7-fold higher ($p<0.0005$ for both) than in plasma of healthy donors (FIG. 7). Mean values±Standard Deviation are shown at the figure. The fluorescence was expressed in counts per second (CPS). Significant increase of the fragments was revealed by using IBP3-IBP144 and IBP182-IBP163 sandwich pairs (FIG. 7).

Example 8. Follow-Up Study of IGFBP-4 Fragments for Major Adverse Cardiac Events Prediction Using Sandwich Immunoassays Specific to IGFBP-4 Proteolytic Fragment For this study samples were obtained from patients at the time of admission at emergency department with chest pain/tightness.

Patients were eligible for study inclusion if they had symptoms of ischemia mainly expressed in specific chest pain of cardiac type that was classified by experienced cardiologist. 166 patients were included in this study. Venous blood from patients was collected into $K_3$EDTA-containing Vacuette tubes (Greiner Bio-One) and centrifuged at 3000 g for 15 min at 4° C. Plasma samples were stored at −70° C. All patients were followed up prospectively for 6 months from the day of study entry (when they had all of the baseline assessments) or until death. The registered primary endpoints included major adverse cardiac events (MACE) that comprises of nonfatal myocardial infarction, cardiac death. Combined endpoints included MACE and all-cause deaths (MACEACD). A total of 166 patients had a complete follow-up (100%). There were 17 MACE cases and 31 MACEACD cases.

ROC curve analysis was performed to investigate the predictive value of NT-, CT-IGFBP-4, full-length IGFBP-4 and their ratios. MACE endpoints at 6 months were the events of interest. The best cut-off of NT- and CT-IGFBP-4 in predicting MACE and MACEACD endpoints were derived from the receiver operator curves (ROC curves) and was defined as the value that gave the best combination of sensitivity and specificity.

In the present invention detection of proteolytic fragments of IGFBP-4 in the plasma samples of acute chest pain patients was carried out using sandwich immunoassays specific to proteolytic fragments. Blood of 166 patients were tested by fragment-specific sandwich immunoassays IBP3-IBP144 (for NT-IGFBP-4) and IBP182-IBP163 (for CT-IGFBP-4).

For the sandwich immunoassay measurements capture antibody IBP3 and IBP182, 2 µg per well in 0.1 ml of phosphate buffer saline, was incubated in 96-well immunoassay plates for 30 min at room temperature upon constant shaking. After washing with buffer A, 0.1 ml of patients' plasma samples diluted 1:5 with the Assay buffer were added to the plates. Plates were incubated for 30 min at room temperature with constant shaking. After washing with buffer A 0.1 ml detection antibody IBP144 and IBP163 in the Assay buffer was added. The plates were incubated for 30 min at room temperature with constant shaking. After washing with buffer A, 0.2 ml of Enhancement solution per well was added and incubated for 3 min at room temperature with gentle shaking. Fluorescence of Eu3+ was measured using a Victor 1420 multilabel counter (Wallac-Perkin Elmer).

Figure 8A:
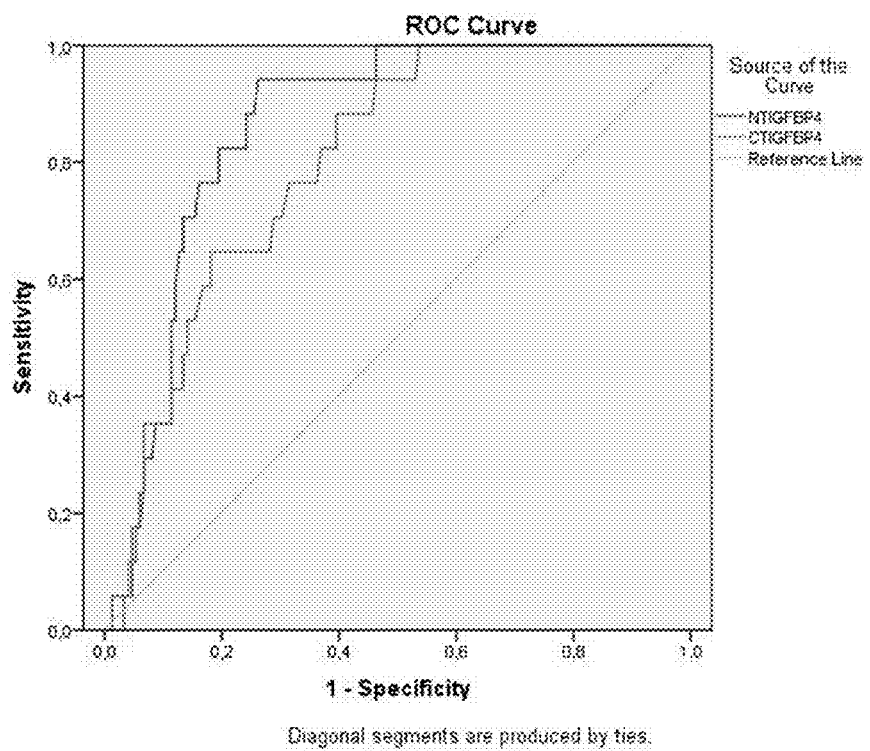
FIGS. 8A and 8B. ROC curves for NT-IGFBP-4 and CT-IGFBP-4 measured by sandwich immunoassays IBP3-IBP144 and BP182-IBP163, respectively. A—MACE prediction, B—MACEACD prediction.
Figure 8B:
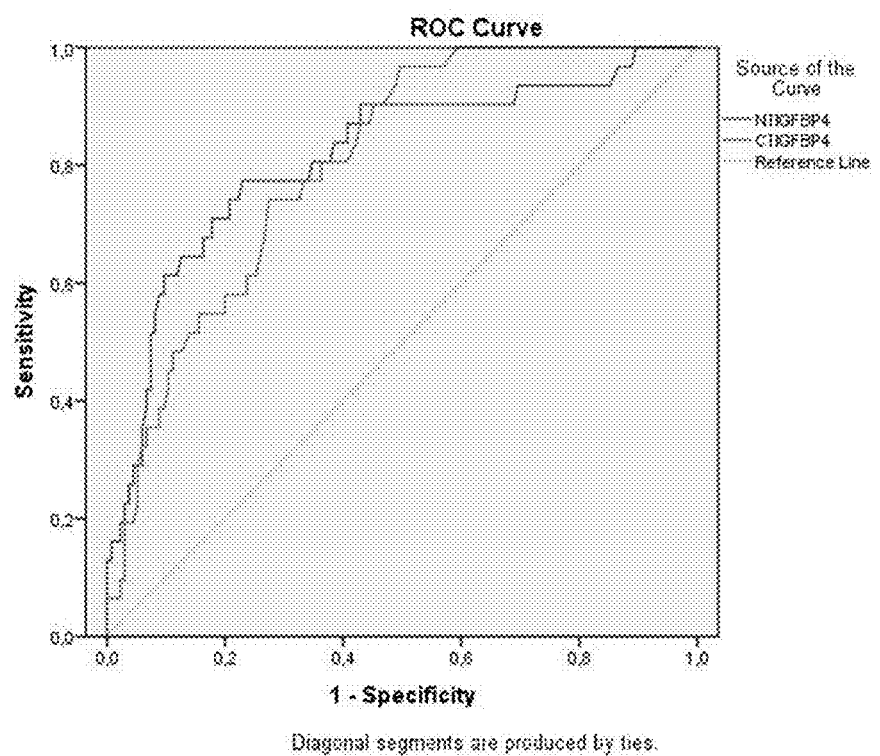

NT- and CT-IGFBP-4 concentrations ranged 7-2553 and 12-564 µg/L, respectively. The ability of NT- and CT-IGFBP-4 and their ratios to predict the MACE at 6 months was investigated by ROC analysis (FIG. 8). Results of area under ROC curves (ROC AUC) for NT- and CT-IGFBP-4 assays were 0.861 ($P<0.001$) and 0.800 ($P<0.001$) respectively that shows NT and CT-IGFBP-4 as strong predictors of the MACE (FIG. 8A). As well NT- and CT-IGFBP-4 were strong predictors of MACEACD: ROC AUC 0.814 ($P<0.001$) and 0.803 ($P<0.001$), respectively (FIG. 8B). Cut-off value for present study was estimated at 214 µg/L for NT-IGFBP-4 and 124 µg/L for CT-IGFBP-4.

Both NT- and CT-IGFBP-4 appeared to be strong predictors of MACE and MACEACD in the patients with acute chest pain at 6-months follow-up (FIG. 8).

For 114 samples randomly selected from this collection cardiac troponin I was measured. This part of the collection contained 10 MACE cases in 6 months follow-up period. In this part of the collection results of ROC AUC for cardiac troponin I were 0.686 ($P=0.053$) and 0.8 ($P=0.002$) for CT-IGFBP-4. The prediction ability of the combined model based on both cardiac troponin I and CT-IGFBP-4 showed ROC AUC 0.848 ($P<0.001$) that indicated the added value of combined cardiac troponin I and CT-IGFBP-4 model as strong predictors of the MACE over the separate biomarkers.

Example 9. Follow-Up Study of IGFBP-4 Fragments for Major Adverse Cardiac Events Prediction Using Differential Sandwich Immunoassays For this study part of the collection of blood samples described in Example 8 was used. This randomly selected part included 66 patients. Six MACE cases were registered for this part of the collection during 6 moths follow-up.

Detection of proteolytic fragments of IGFBP-4 in the plasma samples of acute chest pain patients was carried out using sandwich immunoassays specific to total IGFBP-4 IBP17-IBP180 and IBP185-IBP190 and immunoassays specific to full-length IGFBP-4 IBP185-IBP180 and IBP185-IBP154. Sandwich immunoassay measurements were performed as described in Example 8.

The median full-length IGFBP-4 concentrations (interquartile range) of the study cohort was 822 (652-1013) µg/L, concentrations range 441-1865 µg/L. The concentrations range of total IGFBP-4 concentrations, measured by CT-specific assay and NT-specific assay were 159-1124 and 46-1968 µg/L, respectively. Quantity of NT-IGFBP-4 fragment was calculated as difference between amount of total IGFBP-4 (full-length and NT-IGFBP-4 fragments assay, IBP17-IBP180) and full-length IGFBP-4. Quantity of CT-IGFBP-4 fragment was calculated as difference between amount of total IGFBP-4 (full-length and CT-IGFBP-4 fragments assay, IBP185-IBP190) and full-length IGFBP-4.

Figure 9:
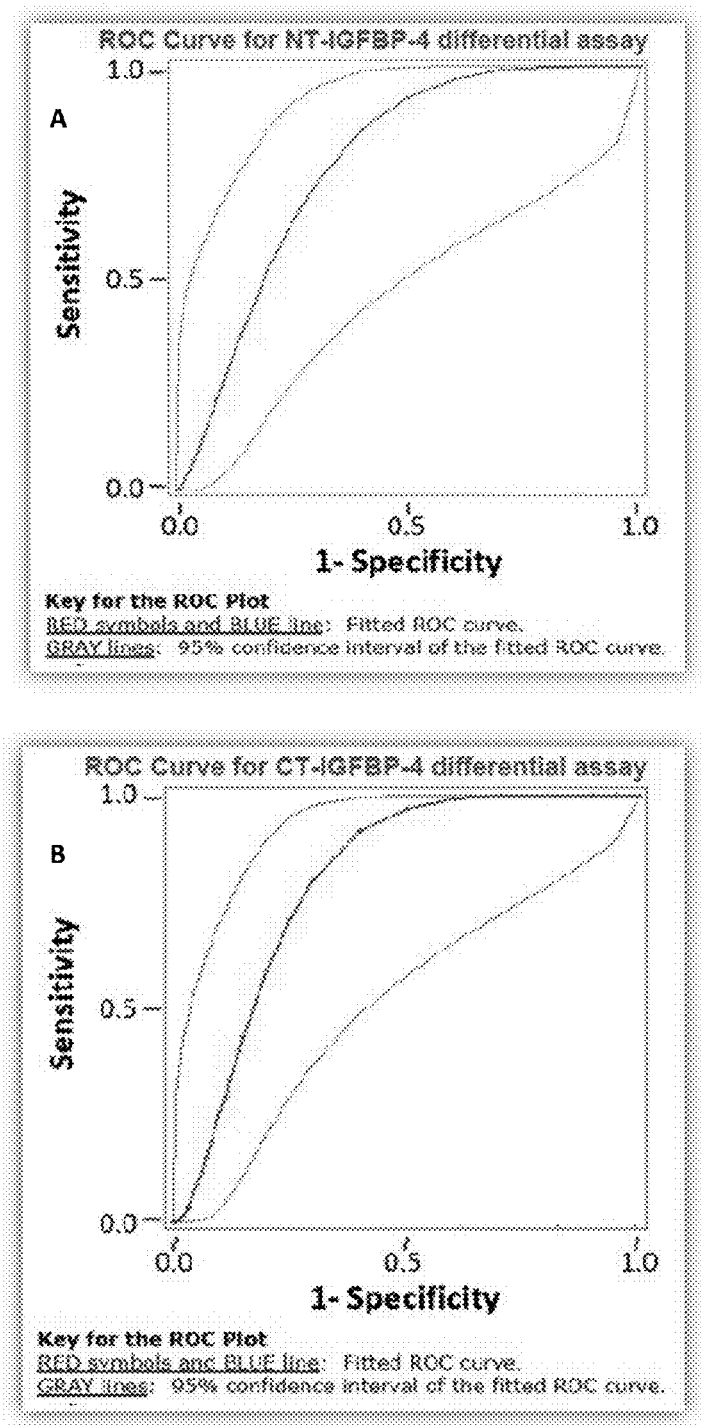
FIGS. 9A and 9B. A—ROC curves for NT-IGFBP-4 proteolytic fragment measured by differential immunoassay (difference between total IGFBP-4 measured by IBP17-IBP180, and full-length IGFBP-4 measured by IBP185-IBP154), B—ROC curves for CT-IGFBP-4 proteolytic fragment by differential immunoassay (difference between total IGFBP-4 measured by IBP185-IBP190, and full-length IGFBP-4 measured by IBP185-IBP154).

Results of ROC AUC for NT- and CT-IGFBP-4 assays were 0.77 (P<0.01) and 0.8 (P<0.01) respectively that shows NT and CT-IGFBP-4 as strong predictors of the MACE (FIG. 9). The ability of NT- and CT-IGFBP-4 measured by differential assay to predict the MACE at 6 months was investigated by ROC analysis (FIGS. 9A and 9B, respectively).

Example 10. Generation of Mouse Monoclonal Antibodies Specific to Novel Proteolysis-Mediated Epitope of IGFBP-5

Synthetic Peptide Obtained for Mice Immunization:
IGFBP-5 Peptide-4: CKAEAVKKDRRKKLTQS (SEQ ID NO: 9)

IGFBP-5 Peptide-4 was synthesized using solid-phase Fmoc chemistry as described above. IGFBP-5 Peptide-4 contained the amino acid sequence identical to IGFBP-5 fragment 128-143 with one additional cysteine residue from the N-terminus. Preparation of conjugates of the peptide with carrier proteins (BSA and ovalbumin) was performed by using sulfo-SMCC as described above.

Immunization of Mice with Peptide-(Carrier Protein) Conjugates

12 BALB/c mice were immunized five times with peptide-protein conjugates. First immunization: intraperitoneally 0.2 ml of 10 µg BSA-IGFBP-5-Peptide-4 in PBS with 60% Freund's complete adjuvant; Second immunization: on day 30, intraperitoneally 0.2 ml of 5 µg BSA-IGFBP-5-Peptide-4 in PBS with 60% Freund's incomplete adjuvant; Third immunization: on day 60, intraperitoneally 0.2 ml of 2.5 µg BSA-IGFBP-5-Peptide-4 in PBS.

Twenty days after third immunization mice with the highest titer of peptide-specific antibodies were selected for the last immunizations and hybridization. Mice were intravenously injected with 0.2 ml of 10 µg BSA-IGFBP-5-Peptide-4 in PBS. Intravenous injections were repeated next day at the same protocol (fifth immunization). Then two days after the fifth immunization, spleens of immunized mice were sterilely isolated and homogenized tissue was fused with the mouse myeloma cell line sp2/0 as described previously (Köhler and Milstein, 1975, 1976; Köhler et al., 1976; Hammerling et al., 1981).

Conditioned media of growing hybridomas was screened for antibodies by enzyme linked immunosorbent assay (ELISA). Hybridomas that produced antibodies specific to BSA-IGFBP-5-Peptide-4 were selected by ELISA with ovalbumin-IGFBP-5-Peptide-4, respectively, used as preadsorbed antigens. Human recombinant IGFBP-5 expressed in HEK 293F cells was used as well as a preadsorbed antigen for the additional test. For the assay 50 ng/0.1 ml PBS per well of ovalbumin-IGFBP-5-Peptide-4, or human recombinant IGFBP-5 were adsorbed onto the immunoassay polystyrene plates (obtained from Corning, Cambridge, Mass.). After 40 min of antigen sorption the plates were washed two times and blocked for 10 min with PBS, containing detergent Tween 20, 0.1% (PBST). Then the plates were incubated with 0.05 ml of conditioned media collected from growing hybridomas for 30 min and washed two times with PBST. Mouse antibodies bound to preadsorbed antigens were revealed by 30 min incubation with secondary anti-mouse IgG polyclonal antibodies, conjugated with HRP, 0.1 ml of 1:1000 dilution in PBST per well. Secondary antibodies were from Sigma Chemicals, St. Louise, Mo. After the incubation with secondary antibodies the plates were washed with PBST six times and 3,3',5,5'-tetramethyl benzidine (TMB) peroxidase substrate, containing 0.03% hydrogen peroxide, was added. The reaction was stopped after 15 minutes of incubation by adding 0.1 ml of 0.5 M phosphoric acid and absorbance in wells was measured at 450 nm. The measurement of the absorbance was performed with the Labsystems Multiscan microplate reader (Labsystems, Finland).

Hybridomas producing antibodies specific to appropriate peptide, conjugated with ovalbumin (Absorbance at described above conditions at 450 nm>0.5 over background), and at the same time not reacting with human recombinant IGFBP-5 (Absorbance at 450 nm<0.025 over background), were selected for further work. Such hybridomas were cloned by limiting dilution. Hybridoma clones secreting the monoclonal antibodies of interest were grown in Dulbecco's modified Eagle's medium (DMEM), containing 10% fetal bovine serum (HyClone Laboratories, Logan, Utah).

Production and affinity purification of antibodies were carried out as described above.

Investigation of Specificity of Monoclonal Antibodies

Figure 10:
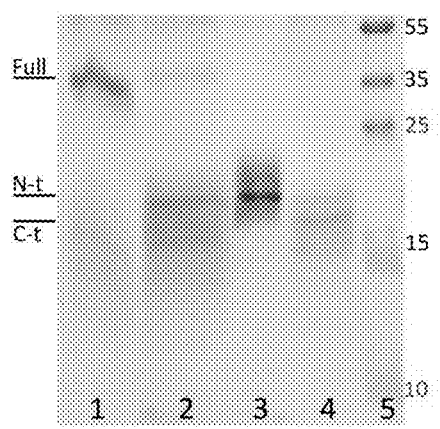
FIG. 10. PAPP-A-dependent cleavage of IGFBP-5 determined by sodium dodecyl sulphate polyacrylamide gel electrophoresis with the Coomassie Blue R-250 staining.
Lane 1, IGFBP-5 (1 µg per lane) without PAPP-A;
Lane 2, specifically cleaved IGFBP-5 with recombinant PAPP-A;
Lane 3, recombinant NT-IGFBP-5 (1 µg);
Lane 4, recombinant CT-IGFBP-5 (1 µg);
Lane 5, Molecular weight standards; shown in kDa.

To confirm the specificity of selected monoclonal antibodies IGFBP-5 proteolytic fragments were obtained. PAPP-A-dependent proteolytic reaction was performed according to conditions described below. Twelve µg of human recombinant IGFBP-5 was incubated in 0.12 ml of 50 mM Tris-HCl, pH 7.5, in the presence of 2 mM $CaCl_2$. 120 ng of human recombinant PAPP-A (HyTest, Turku, Finland), and 0.5 microliters protease inhibitors cocktail (obtained from Sigma Chemicals, St. Louise, Mo.). The reaction was carried out for 40 minutes at 37° C., and was stopped by freezing the sample at −70° C. The degree of PAPP-A-dependent cleavage of IGFBP-5 was determined by sodium dodecyl sulphate polyacrylamide gel electrophoresis with the following Coomassie Blue R-250 staining (FIG. 10). Specificity studies of selected monoclonal antibodies to IGFBP-5 proteolytic fragments were performed in indirect ELISA using affinity-purified antibodies. Ten ng of full-length recombinant IGFBP-5 or IGFBP-5 fragments produced by PAPP-A-dependent cleavage (preparation described above) were sorbed on polystyrene plate. After 40 min of incubation the plates were washed two times and blocked for 10 min with PBS, containing detergent Tween 20, 0.1% (PBST). Selected MAbs (10 µg/ml) were incubated for 30 min at room temperature with shaking and after that washed two times with PBST. Specifically bound antibodies were detected by anti-mouse IgG polyclonal antibodies, conjugated with HRP, 0.1 ml of 1:1000 dilution in PBST per well. Secondary antibodies were from Sigma Chemicals, St. Louise, Mo. After incubation with secondary antibodies the plates were washed with PBST six times and 3,3',5,5'-tetramethyl benzidine (TMB)-containing peroxidase substrate, supplemented with 0.03% hydrogen peroxide, was added. The reaction was stopped after 15 minutes of incubation by adding 0.1 ml of 0.5 M phosphoric acid and absorbance was measured at 450 nm. One monoclonal antibody specific to proteolytic fragments of IGFBP-5, produced by PAPP-A-dependent cleavage, and having cross-reactivity to intact IGFBP-5 less than 5% was finally selected: IBPF72 (FIG. 2). IBPF72 was of IgG isotype.

Example 11. Generation of Mouse Monoclonal Antibodies Specific to Intact IGFBP-5

Synthetic Peptide Obtained for Mice Immunization:
IGFBP-5 Peptide-2: CLNEKSYREQVKIERDSREHE (SEQ ID NO: 10)

IGFBP-5 Peptide-2 was synthesized using solid-phase Fmoc chemistry as described above.

IGFBP-5 Peptide-2 contained the amino acid sequence identical to IGFBP-5 fragment 80-100. Preparation of conjugates of the peptide with carrier protein (BSA) was performed by using sulfo-SMCC as described above.

Immunization of mice with peptide-(carrier protein) conjugates. Twelve BALB/c mice were immunized five times with peptide-protein conjugate. First immunization: intraperitoneally 0.2 ml of 10 μg BSA-IGFBP-5-Peptide-2 in PBS with 60% Freund's complete adjuvant; Second immunization: on day 30, intraperitoneally 0.2 ml of 5 μg BSA-IGFBP-5-Peptide-2 in PBS with 60% Freund's incomplete adjuvant; Third immunization: on day 60, intraperitoneally 0.2 ml of 2.5 μg BSA-IGFBP-5-Peptide-2 in PBS.

Twenty days after third immunization mice with the highest titer of peptide-specific antibodies were selected for the last immunizations and hybridization. Mice were intravenously injected with 0.2 ml of 10 μg BSA-IGFBP-5-Peptide-2 in PBS. Intravenous injections were repeated next day at the same protocol (fifth immunization). Then two days after the fifth immunization, spleens of immunized mice were sterilely isolated and homogenized tissue was fused with the mouse myeloma cell line sp2/0 as described previously (Köhler and Milstein, 1975, 1976; Köhler et al., 1976; Hammerling et al., 1981).

Conditioned media of growing hybridomas was screened for IGFBP-5-specific antibodies using ELISA method. Hybridomas producing antibodies specific to intact IGFBP-5 were selected by means of indirect ELISA. For the assay 50 ng/0.1 ml PBS per well of full-length human recombinant IGFBP-5 were sorbed on the immunoassay polystyrene plates.

After 40 min of incubation the plates were washed two times and blocked for 10 min with PBS, containing detergent Tween 20, 0.1% (PBST). Then the plates were incubated for 30 min with 0.05 ml of conditioned media collected from wells containing growing hybridomas. After incubation the plates were washed two times with PBST. After washing the plates were incubated with 0.1 ml of per well of secondary anti-mouse IgG polyclonal antibodies, conjugated with HRP (1:1000 dilution in PBST) for 30 min. After incubation with secondary antibodies the plates were washed with PBST six times and peroxidase substrate, containing TMB and 0.03% hydrogen peroxide, was added. The reaction was stopped after 15 minutes of incubation by adding 0.1 ml of 0.5 M phosphoric acid and the absorbance in wells was measured at 450 nm. Hybridomas producing antibodies specific to full-length IGFBP-5 (absorbance at described above conditions at 450 nm>0.5 over background) were cloned by limiting dilution method. Hybridoma clones secreting the monoclonal antibodies of interest were cultivated in DMEM, containing 10% fetal bovine serum.

Production and affinity purification of antibodies were carried out as described above. The group of monoclonal antibodies specific to intact IGFBP-5 was finally selected: IBPF15, IBPF16.

Figure 11:
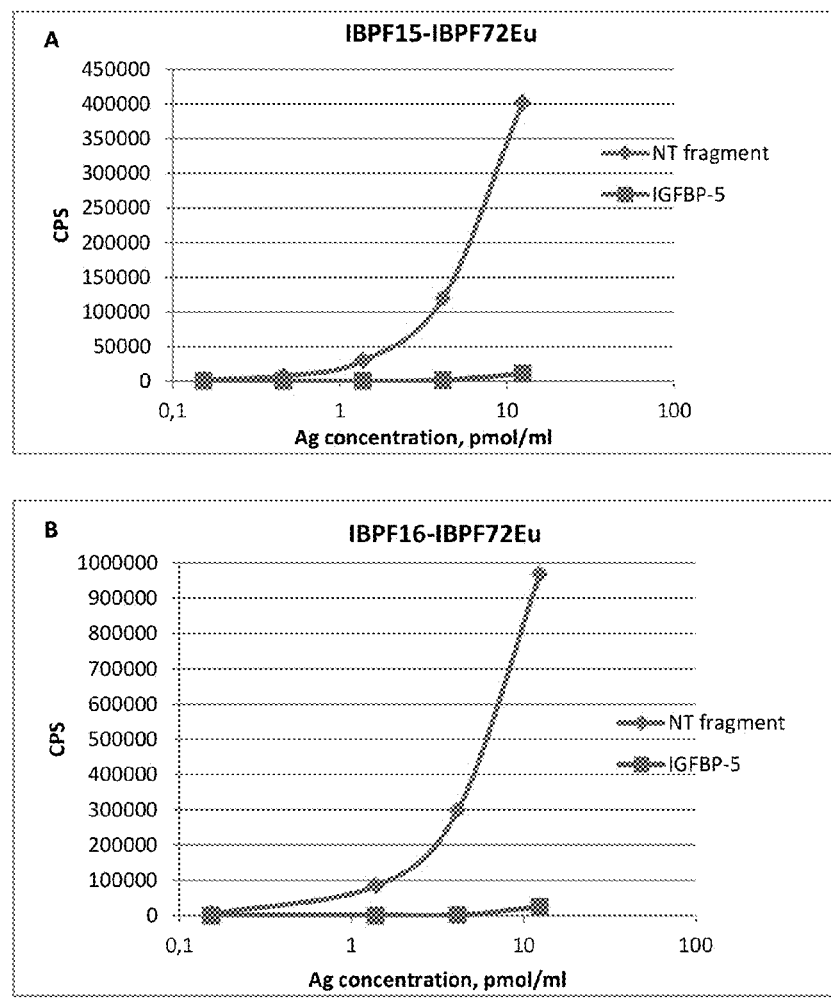
FIGS. 11A and 11B. Calibration curves of sandwich immunoassays specific to NT-IGFBP-5 proteolytic fragments (A, IBPF15-IBPF72 and B, IBPF16-IBPF72) and their crossreaction with full-length IGFBP-5. Antigen concentration of 1 pmol/ml is corresponded to 16.1 ng/ml of NT-IGFBP-5 or 28.6 ng/ml of full-size IGFBP-5.

Example 12. Design of Sandwich Immunoassays for Quantification of IGFBP-5 Fragments Specificity of affinity-purified monoclonal antibody IBPF72 was also checked in sandwich immunoassays (FIG. 11). IBPF72 were tested with monoclonal antibodies specific to the intact (full-length) IGFBP-5 to develop sandwich immunoassays for specific determination of NT-IGFBP-5 regardless of the presence of intact full-length IGFBP-5. Two sandwich assays utilizing IBPF72 monoclonal antibody specific to N-terminal proteolytic fragment of IGFBP-5 (cross-reaction with full-length molecule less than 5% in indirect ELISA) and another MAb, recognizing intact IGFBP-5, were developed. To perform sandwich fluorescent immunoassays, we used detection MAbs labeled with stable Eu3+ chelate as described by Hyytiä et al., 2010. Capture antibodies in this assay were specific to intact IGFBP-5, whereas detection antibodies were specific to proteolytic neo-epitopes of IGFBP-5. Capture antibodies (IBPF15 or IBPF16), 1.5 μg per well in 100 μL of phosphate buffer saline, were incubated in 96-well immunoassay plates for 30 min at room temperature upon constant shaking. The plates were washed with 10 mM Tris-HCl (pH 7.8) buffer, supplemented by 0.15 M NaCl, 0.025% Tween 20 and 0.5 g/L NaN$_3$ (buffer A). After washing 0.05 ml of assay buffer (50 mM Tris-HCl buffer, pH 7.7, 9 g/L NaCl, 0.01% Tween 40, 0.5% BSA and 0.5 g/L NaN$_3$), containing different concentrations of full-length human recombinant IGFBP-5 or recombinant NT-IGFBP-5 fragment and 0.05 ml of the solution (4 mg/L) of detection antibodies (IBPF72) in the Assay buffer were added. The plates were incubated for 30 min at room temperature with constant shaking. After washing with buffer A, 0.2 ml of Enhancement solution (1.75 M NaSCN, 1 M NaCl, 5% glycerol, 20% 1-propanol, 5 mM Na$_2$CO$_3$, 50 mM glycine-NaOH, pH 10.0) per well ware added and incubated for 3 min at room temperature with gentle shaking. Fluorescence of Eu3+ was measured on a Victor 1420 multilabel counter (Wallac-Perkin Elmer). The fluorescence was expressed in counts per second (CPS). Developed sandwich immunoassays were able to detect only NT-IGFBP-5 produced by PAPP-A-dependent cleavage (or recombinant N-terminal fragment of IGFBP-4) and had no cross-reaction (or less than 5%) with full-length IGFBP-5. Two pairs specific to NT-IGFBP-5 were IBPF15—IBPF72 and IBPF16-IBPF72 (FIGS. 11A and 11B, respectively).

Example 13. Follow-Up Study of NT-IGFBP-5 for Major Adverse Cardiac Events Prediction Using Sandwich Immunoassays Specific to NT-IGFBP-5

Patients admitted at emergency department with chest pain/tightness were included in this study. Also the patients with diagnosed unstable angina or ischemic heart disease were included.

276 patients were included in this study. Venous blood from patients was collected into K$_3$EDTA-containing Vacuette tubes (Greiner Bio-One) and centrifuged at 3000 g for 15 min at 4° C. Plasma samples were stored at −70° C. All patients were followed up prospectively for 6 months from the day of study entry (when they had all of the baseline assessments) or until death. The registered primary endpoints included major adverse cardiac events (MACE) that comprises of nonfatal myocardial infarction, cardiac death. Only patients who had follow-up information were included in the study. There were 24 MACE endpoints during the follow-up.

Concentration of NT-IGFBP-5 was measured by IBPF15-IBPF72 and IBPF16-IBPF72 in all samples of patients with MACE cases as well as in 24 randomly selected from the group of patients without MACE cases. ROC curve analysis was performed to investigate the predictive value of NT-IGFBP-5.

For the sandwich immunoassay measurements capture antibody IBPF15 or IBPF16, 1.5 µg per well in 0.1 ml of phosphate buffer saline, was incubated in 96-well immunoassay plates for 45 min at room temperature upon constant shaking. After washing with buffer A, 0.05 ml of patients' plasma samples diluted 1:2 with the Assay buffer and 0.05 ml of detection antibody IBPF72 in the Assay buffer were added. The plates were incubated for 40 min at room temperature with constant shaking. After washing with buffer A, 0.2 ml of Enhancement solution per well was added and incubated for 3 min at room temperature with gentle shaking. Fluorescence of Eu3+ was measured using a Victor 1420 multilabel counter (Wallac-Perkin Elmer).

Figure 12:
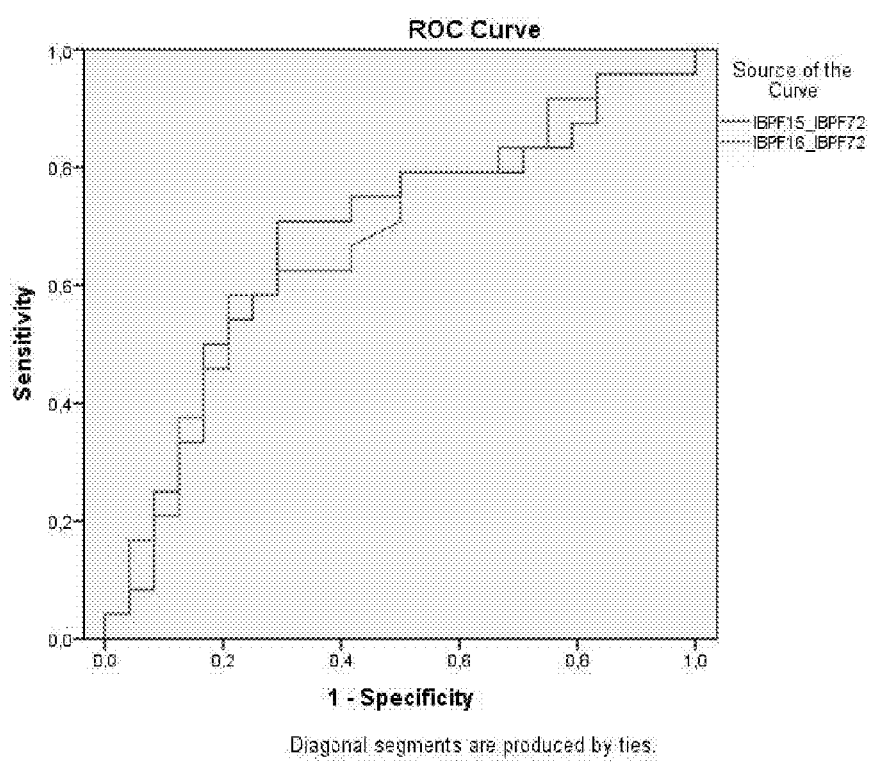
FIG. 12. Blue line-ROC curves for NT-IGFBP-5 proteolytic fragment measured by sandwich immunoassay IBPF15-IBPF72, green line—ROC curves for NT-IGFBP-5 proteolytic fragment measured by sandwich immunoassay IBPF16-IBPF72.

NT-IGFBP-5 concentrations ranged 15.4-83.3 µg/L. The ability of NT-IGFBP-5 to predict MACE at 6 months was investigated by ROC analysis (FIG. 12). Results of area under ROC curves (ROC AUC) for NT-IGFBP-5 assays were 0.68 (P=0.034) for IBPF15-IBPF72 and 0.67 (P=0.039) for IBPF16-IBPF72 that shows NT-IGFBP-5 as strong predictor of the MACE (FIG. 12).

Thus NT-IGFBP-5 appeared to be a predictor of MACE in the patients with acute chest pain, unstable angina or ischemic heart disease at 6-months follow-up.

REFERENCES

Hammerling, G. J., Hammerling, U., and Kearney, J. F. eds., Monoclonal Antibodies and T-Cell Hybridomas, published by Elsevier, North-Holland, New York, 1981; pp. 563-587.

Hyytiä H, Ristiniemi N, Airas L, Pettersson K, Hellman J, Development of an immunoassay for the detection of cystatin C dimers. J Immunol Methods 2010; 355(1-2): 14-20.

Köhler G, Milstein C., Continuous cultures of fused cells secreting antibody of predefined specificity. Nature. 1975; 256(5517):495-7.

Köhler G, Milstein C., Derivation of specific antibody-producing tissue culture and tumor lines by cell fusion. Eur J. Immunol. 1976; 6(7):511-9.

Köhler G, Howe S C, Milstein C., Fusion between immunoglobulin-secreting and nonsecreting myeloma cell lines. Eur J. Immunol. 1976; 6(4):292-5.

Overgaard M T, Haaning J, Boldt H B, Olsen I M, Laursen L S, Christiansen M, Gleich G J, Sottrup-Jensen L, Conover C A, Oxvig C Expression of recombinant human pregnancy-associated plasma protein-A and identification of the proform of eosinophil major basic protein as its physiological inhibitor. Journal of Biological Chemistry, 2000; 275: 31128-31133.

The following gives a list of sequences relevant to the present application. The peptides used for immunization of animals (sequences 7 to 10) are underlined in the larger fragments (sequences 1, 2 and 4). A sequence listing is given separately.

```
SEQ ID NO. 1: (N-terminal of IGFBNP-4):
DEAIHCPPCSEEKLARCRPPVGCEELVREPGCGCCATCALGLGMPCGVYTPR-

CGSGLRCYPPRGVEKPLHTLMHGQGVCMELAEIEAIQESLQPSDKDEGDHPN-

NSFSPCSAHDRRCLQKHFAKIRDRSTSGGKM

SEQ ID NO. 2: (C-terminal of IGFBP-4):
KVNGAPREDARPVPQGSCQSELHRALERLAASQSRTHEDLYIIPIPNCDRNGNFHPKQ-

CHPALDGQRGKCWCVDRKTGVKLPGGLEPKGELDCHQLADSFRE

SEQ ID NO 3: (IGFBP-4)
DEAIHCPPCSEEKLARCRPPVGCEELVREPGCGCCATCALGLGMPCGVYTPRCGS-

GLRCYPPRGVEKPLHTLMHGQGVCMELAEIEAIQESLQPSDKDEGDHPNNSFSPCS-

AHDRRCLQKHFAKIRDRSTSGGKMKVNGAPREDARPVPQGSCQSELHRALERLAA-

SQSRTHEDLYIIPIPNCDRNGNFHPKQCHPALDGQRGKCWCVDRKTGVKLPGGLEPK-

GELDCHQLADSFRE

SEQ ID NO 4: (N-terminal of IGFBP-5):
LGSFVHCEPCDEKALSMCPPSPLGCELVKEPGCGCCMTCALAEGQSCGVYTER-

CAQGLRCLPRQDEEKPLHALLHGRGVCLNEKSYREQVKIERDSREHEEPTTSEMAEE-

TYSPKIFRPKHTRISELKAEAVKKDRRKKLTQS

SEQ ID NO 5: (C-terminal of IGFBP-5):
KFVGGAENTAHPRIISAPEMRQESEQGPCRRHMEASLQELKASPRMVPRAVYLPNCDR-

KGFYKRKQCKPSRGRKRGICWCVDKYGMKLPGMEYVDGDFQCHTFDSSNVE

SEQ ID NO 6: (IGFBP-5):
LGSFVHCEPCDEKALSMCPPSPLGCELVKEPGCGCCMTCALAEGQSCGVYTERCAQ-

GLRCLPRQDEEKPLHALLHGRGVCLNEKSYREQVKIERDSREHEEPTTSEMAEETYSP-

KIFRPKHTRISELKAEAVKKDRRKKLTQSKFVGGAENTAHPRIISAPEMRQESEQGPCRR-
```

-continued
HMEASLQELKASPRMVPRAVYLPNCDRKGFYKRKQCKPSRGRKRGICWCVDKYGMKL-

PGMEYVDGDFQCHTFDSSNVE

SEQ ID NO 7: (IGFBP-4 Peptide-1):
CHFAKIRDRSTSGGKM

SEQ ID NO 8: (IGFBP-4 Peptide-2):
KVNGAPREDARPVPQC

SEQ ID NO 9: (IGFBP-5 Peptide-4):
CKAEAVKKDRRKKLTQS

SEQ ID NO 10: (IGFBP-5 Peptide-2):
CLNEKSYREQVKIERDSREHE

The invention claimed is:

1. A cardiac test kit, said kit comprising:
   1) an anti insulin-like growth factor-binding protein 4 (IGFBP-4) fragment antibody that binds to a PAPP-A generated neoepitope on the N-terminal fragment of IGFBP-4 having SEQ ID NO 1, or
   an anti IGFBP-4 fragment antibody that binds to a PAPP-A generated neoepitope on the C-terminal fragment of IGFBP-4 having SEQ ID NO 2, or
   an anti insulin growth factor-binding protein 5 (IGFBP-5) fragment antibody that binds to a PAPP-A generated neoepitope on the N-terminal fragment of IGFBP-5 having SEQ ID NO 4, or
   an anti IGFBP-5 fragment antibody that binds to a PAPP-A generated neoepitope on the C-terminal fragment of IGFBP-5 having SEQ ID NO 5; and
   2) at least one reagent that measures another marker of major adverse cardiovascular event prediction selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), lipo-protein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO).

2. The cardiac test kit according to claim 1, said kit comprising:
   1) the anti IGFBP-4 fragment antibody that binds to the PAPP-A generated neoepitope on the N-terminal fragment of IGFBP-4 having SEQ ID NO 1, or the anti IGFBP-4 fragment antibody that binds to the PAPP-A generated neoepitope on the C-terminal fragment of IGFBP-4 having SEQ ID NO 2; and
   2) the anti IGFBP-5 fragment antibody that binds to the PAPP-A generated neoepitope on the N-terminal fragment of IGFBP-5 having SEQ ID NO 4, or the anti IGFBP-5 fragment antibody that binds to the PAPP-A generated neoepitope on the C-terminal fragment having of IGFBP-5 having SEQ ID NO 5.

3. The cardiac test kit according to claim 1, said kit further comprising one or more reagents that measure another marker of major adverse cardiovascular event prediction selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), Lipo-protein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO).

4. A method for executing a cardiac testing panel for a human individual comprising:
   contacting blood plasma or serum from an individual with an isolated antibody that specifically binds to a PAPP-A generated neoepitope on the N-terminal fragment of IGFBP-4 having SEQ ID NO: 1, and detecting an amount of the N-terminal fragment of IGFBP-4 having SEQ ID NO 1 that bound to the antibody, or
   contacting blood plasma or serum from an individual with an isolated antibody that specifically binds to a PAPP-A generated neoepitope on the C-terminal fragment of IGFBP-4 having SEQ ID NO: 2, and detecting an amount of the C-terminal fragment of IGFBP-4 having SEQ ID NO 2 that bound to the antibody, or
   contacting blood plasma or serum from an individual with an isolated antibody that specifically binds to a PAPP-A generated neoepitope on the N-terminal fragment of IGFBP-5 having SEQ ID NO: 4, and detecting an amount of the N-terminal fragment of IGFBP-5 having SEQ ID NO 4 that bound to the antibody, or
   contacting blood plasma or serum from an individual with an isolated antibody that specifically binds to a PAPP-A generated neoepitope on the C-terminal fragment of IGFBP-5 having SEQ ID NO: 5, and detecting an amount of the C-terminal fragment of IGFBP-5 having SEQ ID NO 5 that bound to the antibody, and
   assaying for another at least one cardiac marker, selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NTproBNP), lipo-protein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO).

5. The method according to claim 4, wherein the amounts of N-terminal fragment or C-terminal fragments of IGFBP-4 or IGFBP-5 detected by said fragment antibodies in said sample is above a 50th percentile of the corresponding fragment found in a population without history of any cardiovascular diseases.

6. A cardiac test kit, said kit comprising:
   1) an anti insulin-like growth factor-binding protein 4 (IGFBP-4) fragment antibody that binds the N-terminal fragment from IGFBP-4 having SEQ ID NO 1,
   2) an anti IGFBP-4 fragment antibody that binds the C-terminal fragment from IGFBP-4 having SEQ ID NO 2; and
   3) at least one reagent that measures another marker of major adverse cardiovascular event prediction selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), Lipo-protein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO),
   wherein antibody 1) is suitable for determination of the amount of intact IGFBP-4+IGFBP-4 N-terminal fragment in the sample,
   wherein said antibody 1) and antibody 2) combined are suitable for determination of the amount of intact IGFBP-4.

7. A cardiac test kit, said kit comprising:
   1) an anti insulin-like growth factor-binding protein 4 (IGFBP-4) fragment antibody that binds the C-terminal fragment from IGFBP-4 having SEQ ID NO 2,
   2) an anti IGFBP-4 fragment antibody that binds the N-terminal fragment from IGFBP-4 having SEQ ID NO 1, and
   3) at least one reagent that measures another marker of major adverse cardiovascular event prediction selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), lipoprotein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO),
   wherein antibody 1) is suitable for determination of the amount of intact IGFBP-4+IGFBP-4 C-terminal fragment in the sample,
   wherein said antibody 1) and antibody 2) combined are suitable for determination of the amount of intact IGFBP-4.

8. A method for executing a cardiac testing panel for a human individual comprising:
   a) contacting blood plasma or serum from an individual with an anti insulin-like growth factor-binding protein 4 (IGFBP-4) fragment antibody that binds the N-terminal fragment from IGFBP-4 (NT-IGFBP-4) having SEQ ID NO 1 for determination of total amount of the NT-IGFBP-4 fragment and intact IGFBP-4 (SEQ ID NO 3) in the sample,
   b) contacting blood plasma or serum from an individual with an anti IGFBP-4 fragment antibody that binds the C-terminal fragment from IGFBP-4 (SEQ ID NO 2) and an anti IGFBP-4 fragment antibody that binds the NT-IGFBP-4 (SEQ ID NO 1) for determination of the amount of the intact IGFBP-4 (SEQ ID NO 3) in the sample,
   c) comparing the amount of said total amount of NT-IGFBP-4 (SEQ ID NO 1) and intact IGFBP-4 (SEQ ID NO 3) as determined in the step a) with the amount of the intact IGFBP-4 (SEQ ID NO 3) as determined in the step b), and
   d) assaying for another at least one cardiac marker, selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), lipoprotein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO).

9. The method according to claim 8, wherein amount of NT-IGFBP-4 (SEQ ID NO 1) in the sample is determined as the difference of the amount of said total amount of NT-IGFBP-4 (SEQ ID NO 1) and intact IGFBP-4 (SEQ ID NO 3) as determined in the step a) and the amount of the intact IGFBP-4 (SEQ ID NO 3) as determined in the step b).

10. A method for executing a cardiac testing panel for a human individual comprising:
   a) contacting blood plasma or serum from an individual with an anti insulin-like growth factor-binding protein 4 (IGFBP-4) fragment antibody that binds the C-terminal fragment from IGFBP-4 (CT-IGFBP-4) having SEQ ID NO 2 for determination of total amount of CT-IGFBP-4 and intact IGFBP-4 (SEQ ID NO 3) in the sample,
   b) contacting blood plasma or serum from an individual with an anti IGFBP-4 fragment antibody that binds the C-terminal fragment from IGFBP-4 (SEQ ID NO 2) and an anti IGFBP-4 fragment antibody that binds the NT-IGFBP-4 (SEQ ID NO 1) for determination of the amount of the intact IGFBP-4 (SEQ ID NO 3) in the sample,
   c) comparing the amount of said total amount of CT-IGFBP-4 (SEQ ID NO 2) and intact IGFBP-4 (SEQ ID NO 3) as determined in the step a) with the amount of the intact IGFBP-4 (SEQ ID NO 3) as determined in the step b), and
   d) assaying for another at least one cardiac marker, selected from the group consisting of cholesterol fraction, C-Reactive Protein (CRP), cardiac troponin I, cardiac troponin T, B-type natriuretic peptide (BNP), BNP precursor peptide (proBNP), N-terminal proBNP (NT-proBNP), lipoprotein associated phospholipase A2 (Lp-PLA2), placental growth factor (PlGF), estimated glomerular filtration rate (eGFR), homocysteine (HCY), choline, ischemia modified albumin (IMA), soluble CD40 ligand (sCD40L) and myeloperoxidase (MPO).

11. The method according to claim 10, wherein amount of CT-IGFBP-4 (SEQ ID NO 2) in the sample is determined as the difference of the amount of said total amount of CT-IGFBP-4 (SEQ ID NO 2) and intact IGFBP-4 (SEQ ID NO 3) as determined in the step a) and the amount of the intact IGFBP-4 (SEQ ID NO 3) as determined in the step b).

* * * * *

```
                        SEQUENCE LISTING

<160> NUMBER OF SEQ ID NOS: 12

<210> SEQ ID NO 1
<211> LENGTH: 135
<212> TYPE: PRT
<213> ORGANISM: Homo sapiens

<400> SEQUENCE: 1

Asp Glu Ala Ile His Cys Pro Pro Cys Ser Glu Glu Lys Leu Ala Arg
1               5                   10                  15

Cys Arg Pro Pro Val Gly Cys Glu Glu Leu Val Arg Glu Pro Gly Cys
            20                  25                  30

Gly Cys Cys Ala Thr Cys Ala Leu Gly Leu Gly Met Pro Cys Gly Val
        35                  40                  45

Tyr Thr Pro Arg Cys Gly Ser Gly Leu Arg Cys Tyr Pro Pro Arg Gly
    50                  55                  60

Val Glu Lys Pro Leu His Thr Leu Met His Gly Gln Gly Val Cys Met
65                  70                  75                  80

Glu Leu Ala Glu Ile Glu Ala Ile Gln Glu Ser Leu Gln Pro Ser Asp
                85                  90                  95

Lys Asp Glu Gly Asp His Pro Asn Asn Ser Phe Ser Pro Cys Ser Ala
            100                 105                 110

His Asp Arg Arg Cys Leu Gln Lys His Phe Ala Lys Ile Arg Asp Arg
        115                 120                 125

Ser Thr Ser Gly Gly Lys Met
    130                 135

<210> SEQ ID NO 2
<211> LENGTH: 102
<212> TYPE: PRT
<213> ORGANISM: Homo sapiens

<400> SEQUENCE: 2

Lys Val Asn Gly Ala Pro Arg Glu Asp Ala Arg Pro Val Pro Gln Gly
1               5                   10                  15

Ser Cys Gln Ser Glu Leu His Arg Ala Leu Glu Arg Leu Ala Ala Ser
            20                  25                  30

Gln Ser Arg Thr His Glu Asp Leu Tyr Ile Ile Pro Ile Pro Asn Cys
        35                  40                  45

Asp Arg Asn Gly Asn Phe His Pro Lys Gln Cys His Pro Ala Leu Asp
    50                  55                  60

Gly Gln Arg Gly Lys Cys Trp Cys Val Asp Arg Lys Thr Gly Val Lys
65                  70                  75                  80
```

```
Leu Pro Gly Gly Leu Glu Pro Lys Gly Glu Leu Asp Cys His Gln Leu
                85                  90                  95
Ala Asp Ser Phe Arg Glu
            100
```

<210> SEQ ID NO 3
<211> LENGTH: 237
<212> TYPE: PRT
<213> ORGANISM: Homo sapiens

<400> SEQUENCE: 3

```
Asp Glu Ala Ile His Cys Pro Pro Cys Ser Glu Glu Lys Leu Ala Arg
1               5                   10                  15
Cys Arg Pro Pro Val Gly Cys Glu Glu Leu Val Arg Glu Pro Gly Cys
            20                  25                  30
Gly Cys Cys Ala Thr Cys Ala Leu Gly Leu Gly Met Pro Cys Gly Val
        35                  40                  45
Tyr Thr Pro Arg Cys Gly Ser Gly Leu Arg Cys Tyr Pro Pro Arg Gly
    50                  55                  60
Val Glu Lys Pro Leu His Thr Leu Met His Gly Gln Gly Val Cys Met
65                  70                  75                  80
Glu Leu Ala Glu Ile Glu Ala Ile Gln Glu Ser Leu Gln Pro Ser Asp
                85                  90                  95
Lys Asp Glu Gly Asp His Pro Asn Asn Ser Phe Ser Pro Cys Ser Ala
            100                 105                 110
His Asp Arg Arg Cys Leu Gln Lys His Phe Ala Lys Ile Arg Asp Arg
        115                 120                 125
Ser Thr Ser Gly Gly Lys Met Lys Val Asn Gly Ala Pro Arg Glu Asp
    130                 135                 140
Ala Arg Pro Val Pro Gln Gly Ser Cys Gln Ser Glu Leu His Arg Ala
145                 150                 155                 160
Leu Glu Arg Leu Ala Ala Ser Gln Ser Arg Thr His Glu Asp Leu Tyr
                165                 170                 175
Ile Ile Pro Ile Pro Asn Cys Asp Arg Asn Gly Asn Phe His Pro Lys
            180                 185                 190
Gln Cys His Pro Ala Leu Asp Gly Gln Arg Gly Lys Cys Trp Cys Val
        195                 200                 205
Asp Arg Lys Thr Gly Val Lys Leu Pro Gly Gly Leu Glu Pro Lys Gly
    210                 215                 220
Glu Leu Asp Cys His Gln Leu Ala Asp Ser Phe Arg Glu
225                 230                 235
```

<210> SEQ ID NO 4
<211> LENGTH: 143
<212> TYPE: PRT
<213> ORGANISM: Homo sapiens

<400> SEQUENCE: 4

```
Leu Gly Ser Phe Val His Cys Glu Pro Cys Asp Glu Lys Ala Leu Ser
1               5                   10                  15
Met Cys Pro Pro Ser Pro Leu Gly Cys Glu Leu Val Lys Glu Pro Gly
            20                  25                  30
Cys Gly Cys Cys Met Thr Cys Ala Leu Ala Glu Gly Gln Ser Cys Gly
        35                  40                  45
Val Tyr Thr Glu Arg Cys Ala Gln Gly Leu Arg Cys Leu Pro Arg Gln
    50                  55                  60
```

```
Asp Glu Glu Lys Pro Leu His Ala Leu Leu His Gly Arg Gly Val Cys
 65                  70                  75                  80

Leu Asn Glu Lys Ser Tyr Arg Glu Gln Val Lys Ile Glu Arg Asp Ser
                 85                  90                  95

Arg Glu His Glu Glu Pro Thr Thr Ser Glu Met Ala Glu Thr Tyr
            100                 105                 110

Ser Pro Lys Ile Phe Arg Pro Lys His Thr Arg Ile Ser Glu Leu Lys
            115                 120                 125

Ala Glu Ala Val Lys Lys Asp Arg Arg Lys Lys Leu Thr Gln Ser
        130                 135                 140
```

<210> SEQ ID NO 5
<211> LENGTH: 109
<212> TYPE: PRT
<213> ORGANISM: Homo sapiens

<400> SEQUENCE: 5

```
Lys Phe Val Gly Gly Ala Glu Asn Thr Ala His Pro Arg Ile Ile Ser
  1               5                  10                  15

Ala Pro Glu Met Arg Gln Glu Ser Glu Gln Gly Pro Cys Arg Arg His
             20                  25                  30

Met Glu Ala Ser Leu Gln Glu Leu Lys Ala Ser Pro Arg Met Val Pro
         35                  40                  45

Arg Ala Val Tyr Leu Pro Asn Cys Asp Arg Lys Gly Phe Tyr Lys Arg
     50                  55                  60

Lys Gln Cys Lys Pro Ser Arg Gly Arg Lys Arg Gly Ile Cys Trp Cys
 65                  70                  75                  80

Val Asp Lys Tyr Gly Met Lys Leu Pro Gly Met Glu Tyr Val Asp Gly
                 85                  90                  95

Asp Phe Gln Cys His Thr Phe Asp Ser Ser Asn Val Glu
            100                 105
```

<210> SEQ ID NO 6
<211> LENGTH: 252
<212> TYPE: PRT
<213> ORGANISM: Homo sapiens

<400> SEQUENCE: 6

```
Leu Gly Ser Phe Val His Cys Glu Pro Cys Asp Glu Lys Ala Leu Ser
  1               5                  10                  15

Met Cys Pro Pro Ser Pro Leu Gly Cys Glu Leu Val Lys Glu Pro Gly
             20                  25                  30

Cys Gly Cys Cys Met Thr Cys Ala Leu Ala Glu Gly Gln Ser Cys Gly
         35                  40                  45

Val Tyr Thr Glu Arg Cys Ala Gln Gly Leu Arg Cys Leu Pro Arg Gln
     50                  55                  60

Asp Glu Glu Lys Pro Leu His Ala Leu Leu His Gly Arg Gly Val Cys
 65                  70                  75                  80

Leu Asn Glu Lys Ser Tyr Arg Glu Gln Val Lys Ile Glu Arg Asp Ser
                 85                  90                  95

Arg Glu His Glu Glu Pro Thr Thr Ser Glu Met Ala Glu Thr Tyr
            100                 105                 110

Ser Pro Lys Ile Phe Arg Pro Lys His Thr Arg Ile Ser Glu Leu Lys
            115                 120                 125

Ala Glu Ala Val Lys Lys Asp Arg Arg Lys Lys Leu Thr Gln Ser Lys
        130                 135                 140
```

Phe Val Gly Gly Ala Glu Asn Thr Ala His Pro Arg Ile Ile Ser Ala
145                 150                 155                 160

Pro Glu Met Arg Gln Glu Ser Glu Gln Gly Pro Cys Arg Arg His Met
            165                 170                 175

Glu Ala Ser Leu Gln Glu Leu Lys Ala Ser Pro Arg Met Val Pro Arg
            180                 185                 190

Ala Val Tyr Leu Pro Asn Cys Asp Arg Lys Gly Phe Tyr Lys Arg Lys
        195                 200                 205

Gln Cys Lys Pro Ser Arg Gly Arg Lys Arg Gly Ile Cys Trp Cys Val
        210                 215                 220

Asp Lys Tyr Gly Met Lys Leu Pro Gly Met Glu Tyr Val Asp Gly Asp
225                 230                 235                 240

Phe Gln Cys His Thr Phe Asp Ser Ser Asn Val Glu
                245                 250

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Cys His Phe Ala Lys Ile Arg Asp Arg Ser Thr Ser Gly Gly Lys Met
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Lys Val Asn Gly Ala Pro Arg Glu Asp Ala Arg Pro Val Pro Gln Cys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide

<400> SEQUENCE: 9

Cys Lys Ala Glu Ala Val Lys Lys Asp Arg Arg Lys Lys Leu Thr Gln
1               5                   10                  15

Ser

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Cys Leu Asn Glu Lys Ser Tyr Arg Glu Gln Val Lys Ile Glu Arg Asp
1               5                   10                  15

Ser Arg Glu His Glu
                20

```
<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

His Phe Ala Lys Ile Arg Asp Arg Ser Thr Ser Gly Gly Lys Met
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Lys Val Asn Gly Ala Pro Arg Glu Asp Ala Arg Pro Val Pro Gln
1               5                   10                  15
```